United States Patent
Osterfeld et al.

(10) Patent No.: US 10,802,089 B2
(45) Date of Patent: Oct. 13, 2020

(54) DEVICES AND METHODS FOR INCREASING MAGNETIC SENSOR SENSITIVITY

(71) Applicant: MagArray, Inc., Milpitas, CA (US)

(72) Inventors: Sebastian J. Osterfeld, Mountain View, CA (US); Heng Yu, Campbell, CA (US)

(73) Assignee: MagArray, Inc., Milpitas, CA (US)

( * ) Notice: Subject to any disclaimer, the term of this patent is extended or adjusted under 35 U.S.C. 154(b) by 433 days.

(21) Appl. No.: 15/151,308

(22) Filed: May 10, 2016

(65) Prior Publication Data

US 2016/0334370 A1 Nov. 17, 2016

Related U.S. Application Data

(60) Provisional application No. 62/160,210, filed on May 12, 2015.

(51) Int. Cl.
  *G01R 33/12* (2006.01)
  *G01N 27/74* (2006.01)
  *G01N 33/543* (2006.01)

(52) U.S. Cl.
  CPC ....... *G01R 33/1269* (2013.01); *G01N 27/745* (2013.01); *G01N 33/543* (2013.01)

(58) Field of Classification Search
  CPC .............. G01R 33/1269; G01N 27/745
  See application file for complete search history.

(56) References Cited

U.S. PATENT DOCUMENTS

| | | |
|---|---|---|
| 7,906,345 B2 | 3/2011 | Wang et al. |
| 2005/0106758 A1 | 5/2005 | Fukumoto et al. |
| 2009/0104707 A1* | 4/2009 | Wang ............... G01N 33/54326 436/86 |
| 2010/0176807 A1* | 7/2010 | Duric .................. G01N 27/745 324/228 |
| 2011/0027901 A1 | 2/2011 | Gaster et al. |
| 2014/0266186 A1 | 9/2014 | Osterfeld et al. |
| 2014/0272719 A1 | 9/2014 | Liu et al. |
| 2016/0076097 A1* | 3/2016 | Esfandyarpour .... C12Q 1/6853 506/38 |

FOREIGN PATENT DOCUMENTS

WO 2013155290 10/2013

OTHER PUBLICATIONS

Edelstein et al. (2000) "The Barc Biosensor Applied to the Detection of Biological Warfare Agents," Biosensors and Bioelectronics, Elsevier Science Ltd, 14 (10, 11): 805-813.
Martins et al. (2010) "Challenges and trends in the development of a magnetoresistive biochip portable platform," Journal of Magnetism and Magnetic Materials, Elsevier, 322 (9-12): 1655-1663.

* cited by examiner

*Primary Examiner* — Sally A Merkling
(74) *Attorney, Agent, or Firm* — Rudy J. Ng; Bozicevic, Field & Francis LLP

(57) ABSTRACT

Provided are magnetic sensors, which include a magnetic sensor element having a sensor surface modification and an inter-element area adjacent to the magnetic sensor element and having an inter-element area surface modification, where the sensor surface modification and the inter-element area surface modification provide a binding surface in the inter-element area. Also provided are devices, systems and methods in which the subject magnetic sensors find use.

27 Claims, 4 Drawing Sheets

DEVICES AND METHODS FOR INCREASING MAGNETIC SENSOR SENSITIVITY

CROSS-REFERENCE TO RELATED APPLICATION

This application claims priority pursuant to 35 U.S.C. § 119(e) to the filing date of U.S. Provisional Patent Application Ser. No. 62/160,210 filed May 12, 2015 the disclosure of which is herein incorporated by reference.

INTRODUCTION

Biomarkers (also called disease signatures) are specific analytes like RNA, DNA and proteins that can be used as surrogates for a mechanism of action, disease state or clinical endpoint. In particular, multiplexed or multimarker approaches may be used in molecular diagnostics and personalized medicine, whose goal is to identify the right treatment for the right patient at the right time and dose, or to detect early complex diseases such as cancer and cardiovascular diseases sensitively and specifically. DNA and protein microarrays have been developed to accommodate a large number of biomarkers.

Certain biomolecules, for example cancer embryonic antigen (CEA), could potentially serve as a diagnostic indicator for early stage cancer. However, many of the proteins which are expected to have diagnostic value are present in the bloodstream at extremely low concentrations, which makes them challenging to quantify with analytical techniques.

Most commercial DNA microarray systems utilize fluorescent labeling (tagging) to quantify biomolecular analytes (targets). They may be of limited sensitivity because they require approximately $10^4$ or more molecules to achieve a useful signal-to-noise ratio and are marginally quantitative because of the optical systems involved, and also because of crosstalk and bleaching. The optical detection systems are usually used in conjunction with amplification techniques such as polymerase chain reaction (PCR) which multiplies the original biomolecules by many orders of magnitude. Alternative microarray technologies with a higher sensitivity may be useful in the field of molecular diagnostics and genomics.

SUMMARY

Provided are magnetic sensors, which include a magnetic sensor element having a sensor surface modification and an inter-element area adjacent to the magnetic sensor element and having an inter-element area surface modification, where the sensor surface modification and the inter-element area surface modification provide a binding surface in the inter-element area. Also provided are devices, systems and methods in which the subject magnetic sensors find use.

In some embodiments, the sensor surface modification and the inter-element area surface modification include different surface modifications.

In some embodiments, the sensor surface modification and the inter-element area surface modification include different chemical compositions.

In some embodiments, the sensor surface modification includes a layer of a metal on a surface of the magnetic sensor element and the inter-element area surface modification includes a layer of a dielectric material on a surface of the inter-element area. In some embodiments, the metal is gold and the dielectric material is silicon dioxide.

In some embodiments, the sensor surface modification includes a layer of a dielectric material on a surface of the magnetic sensor element and the inter-element area surface modification includes a layer of a metal on a surface of the inter-element area. In some embodiments, the dielectric material is silicon dioxide and the metal is gold.

In some embodiments, the inter-element area includes a side surface of the magnetic sensor element having a side surface modification.

In some embodiments, the side surface modification is different from the sensor surface modification.

In some embodiments, the side surface modification is different from the inter-element area surface modification.

In some embodiments, the side surface modification is the same as the inter-element area surface modification.

In some embodiments, the side surface modification has a thickness of 15 nm to 150 nm.

In some embodiments, the sensor surface modification and the inter-element area surface modification each include a layer of a dielectric material and the side surface modification of the magnetic sensor element includes a layer of a metal. In some embodiments, the dielectric material is silicon dioxide and the metal is gold.

In some embodiments, the sensor surface modification includes a cover on a surface of the magnetic sensor element.

In some embodiments, a width of the inter-element area is 0.5 times or more a width of the magnetic sensor element.

In some embodiments, a length of the magnetic sensor element is 1.5 times or more a width of the magnetic sensor element.

In some embodiments, the inter-element area has a depth of 25 nm or more.

In some embodiments, the magnetic sensor element includes a reference layer with a magnetization substantially parallel to a width of the magnetic sensor element.

Aspects of the present disclosure include a magnetic sensor system that includes a magnetic sensor device and a magnetic field source. The magnetic sensor device includes a magnetic sensor array having two or more magnetic sensors each including a magnetic sensor element having a sensor surface modification and an inter-element area adjacent to the magnetic sensor element and having an inter-element area surface modification, where the sensor surface modification and the inter-element area surface modification provide a binding surface in the inter-element area.

In some embodiments, the magnetic sensor system includes a processor configured to obtain an analyte-specific signal from the magnetic sensor device.

Aspects of the present disclosure include a method of evaluating whether an analyte is present in a sample. The method includes contacting a magnetic sensor with a sample to generate a signal and evaluating whether the analyte is present in the sample based on the signal. The magnetic sensor includes a magnetic sensor element having a sensor surface modification and an inter-element area adjacent to the magnetic sensor element and having an inter-element area surface modification, where the sensor surface modification and the inter-element area surface modification provide a binding surface in the inter-element area.

In some embodiments, the method includes magnetically labeling the sample prior to the contacting.

In some embodiments, the evaluating includes obtaining a signal from the magnetic sensor as the magnetically-labeled sample contacts the magnetic sensor.

In some embodiments, the contacting includes applying a magnetic label to the magnetic sensor after contacting the magnetic sensor with the sample.

Aspects of the present disclosure include a kit that includes a magnetic sensor device and a magnetic label. The magnetic sensor device includes a magnetic sensor array having two or more magnetic sensors each including a magnetic sensor element having a sensor surface modification and an inter-element area adjacent to the magnetic sensor element and having an inter-element area surface modification, where the sensor surface modification and the inter-element area surface modification provide a binding surface in the inter-element area.

DETAILED DESCRIPTION

Figure 1:
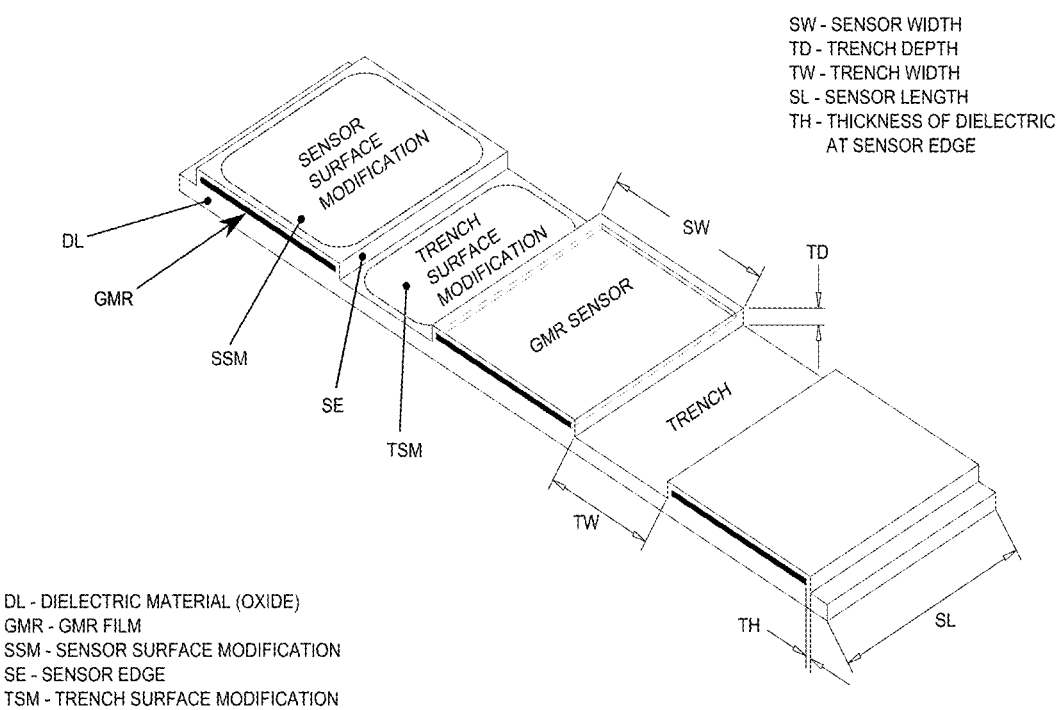
FIG. 1 shows a cross-sectional drawing of a magnetic sensor according to embodiments of the present disclosure.

Provided are magnetic sensors, which include a magnetic sensor element having a sensor surface modification and an inter-element area adjacent to the magnetic sensor element and having an inter-element area surface modification, where the sensor surface modification and the inter-element area surface modification provide a binding surface in the inter-element area. Also provided are devices, systems and methods in which the subject magnetic sensors find use.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following sections, the subject magnetic sensors are described first in greater detail, followed by a description of the magnetic sensor devices, systems and methods in which the subject magnetic sensors find use.

Magnetic Sensors

Aspects of the present disclosure include a magnetic sensor. In some instances, the magnetic sensor is configured to increase sensitivity of the magnetic sensor. For example, the magnetic sensor may be configured to preferentially bind magnetic labels on certain areas of the surface of the magnetic sensor to increase sensitivity of the magnetic sensor to the bound magnetic labels. Increasing the sensitivity of the magnetic sensor may facilitate an increase in the accuracy of the magnetic sensor, and may facilitate the detection of specific analytes in a sample that may be present in the sample at a low concentration.

In certain embodiments, the magnetic sensor includes a magnetic sensor element having a sensor surface modification and an inter-element area adjacent to the magnetic sensor element and having an inter-element area surface modification, where the sensor surface modification and the inter-element area surface modification provide a binding surface (e.g., magnetic label binding surface) in the inter-element area.

In certain embodiments, the magnetic sensor includes a magnetic sensor element. The magnetic sensor element may be a giant magnetoresistive (GMR) element or a tunneling magnetoresistive (TMR) element. For example, the magnetic sensor element may be a spin valve magnetoresistive element or a magnetic tunnel junction (MTJ) magnetoresistive element, each of which are described in additional detail in the sections below.

In certain embodiments, the magnetic sensor element includes a sensor surface modification. The sensor surface modification may be configured to bind to a magnetic label. For instance, the sensor surface modification may be configured to preferentially bind to a magnetic label in a sample being analyzed by the magnetic sensor device. In certain embodiments (and as described in additional detail herein), the sensor surface modification may include an analyte-specific probe (e.g., a surface capture ligand) that specifically binds to a magnetically labeled analyte, thereby indirectly binding a specific analyte to the sensor surface.

In other embodiments, the sensor surface modification may be configured to minimize binding of a magnetic label to the magnetic sensor element. For example, the sensor surface modification may provide a surface on the magnetic sensor element that minimizes binding interactions between the sensor surface and magnetic labels. In certain embodiments, the sensor surface modification may not include an analyte-specific probe (e.g., a surface capture ligand). Stated another way, the sensor surface may be substantially free of an analyte-specific probe (e.g., a surface capture ligand).

In certain embodiments, the sensor surface modification includes a chemical modification. In some instances, the sensor surface modification includes a layer of a metal. For example, the metal may be gold. In some instances, the metal surface (e.g., gold surface) may be modified to bind to a magnetic label. For example, the metal surface (e.g., gold surface) may be configured to preferentially bind to a magnetic label in a sample being analyzed by the magnetic sensor device. In certain embodiments (and as described in additional detail herein), the metal surface modification may include an analyte-specific probe (e.g., a surface capture ligand) that specifically binds to a magnetically labeled analyte, thereby indirectly binding a specific analyte to the metal sensor surface modification.

In other embodiments, the metal surface (e.g., gold surface) may be configured to minimize binding of a magnetic label to the magnetic sensor element. For example, the metal surface (e.g., gold surface) may provide a surface on the magnetic sensor element that minimizes binding interactions between the sensor surface and magnetic labels. In certain embodiments, the metal sensor surface modification may not include an analyte-specific probe (e.g., a surface capture ligand). Stated another way, the metal sensor surface may be substantially free of an analyte-specific probe (e.g., a surface capture ligand).

As described above, the sensor surface modification may include a chemical modification. In some instances, the sensor surface modification includes a layer of a dielectric material. For example, the dielectric material may be silicon dioxide. In some instances, the surface of the dielectric material may be modified to bind to a magnetic label. For example, the surface of the dielectric material may be configured to preferentially bind to a magnetic label in a sample being analyzed by the magnetic sensor device. In certain embodiments (and as described in additional detail herein), the dielectric surface modification may include an analyte-specific probe (e.g., a surface capture ligand) that specifically binds to a magnetically labeled analyte, thereby indirectly binding a specific analyte to the dielectric sensor surface modification.

In other embodiments, the surface of the dielectric material may be configured to minimize binding of a magnetic label to the magnetic sensor element. For example, the surface of the dielectric material may provide a surface on the magnetic sensor element that minimizes binding interactions between the sensor surface and magnetic labels. In certain embodiments, the dielectric sensor surface modification may not include an analyte-specific probe (e.g., a surface capture ligand). Stated another way, the dielectric sensor surface may be substantially free of an analyte-specific probe (e.g., a surface capture ligand).

In some embodiments, the sensor surface modification includes a layer of the sensor surface modification disposed on a surface of the magnetic sensor element. The layer of the sensor surface modification may be a substantially contiguous surface layer. By "contiguous" is meant that the sensor surface modification covers an area without significant voids or discontinuous areas in the layer of the sensor surface modification.

In some cases, the layer of the sensor surface modification may be substantially uniform in thickness. For example, the sensor surface modification may have a thickness ranging from 1 nm to 1000 nm, such as from 5 nm to 750 nm, or 5 nm to 500 nm, or 10 nm to 250 nm, or 10 nm to 200 nm, or 10 nm to 150 nm, or 15 nm to 150 nm, or 15 nm to 100 nm, or 15 nm to 75 nm, or 15 nm to 50 nm. In some cases, the sensor surface modification has a thickness of 15 nm to 150 nm.

In certain embodiments, the magnetic sensor includes an inter-element area adjacent to the magnetic sensor element. The inter-element area may be adjacent to the magnetic sensor element such that one side of the inter-element area is in contact with one side of the magnetic sensor element. For example, a length of an inter-element area may be adjacent to (e.g., in contact with) a length of a magnetic sensor element. In some cases, the inter-element area is adjacent to two magnetic sensor elements. For instance, the inter-element area may be in between two magnetic sensor elements. In some cases, the inter-element area is adjacent to a magnetic sensor element on one side of the inter-element area and adjacent to another magnetic sensor element on an opposing side of the inter-element area. For example, the inter-element area may be coplanar with the adjacent magnetic sensor elements. In these embodiments, the magnetic sensors and adjacent inter-element areas may be arranged in series. In some cases, a plurality of magnetic sensor elements and a plurality of inter-element areas may be arranged in series in an alternating pattern of magnetic sensor elements and inter-element areas. As described above, each magnetic sensor element may be adjacent to one or two inter-element areas on opposing sides of the magnetic sensor element, and each inter-element area may be adjacent to one or two magnetic sensor elements on opposing sides of the inter-element areas.

In certain embodiments, the inter-element area includes an inter-element area surface modification. The inter-element area surface modification may be configured to bind to a magnetic label. For instance, the inter-element area surface modification may be configured to preferentially bind to a magnetic label in a sample being analyzed by the magnetic sensor device. In certain embodiments (and as described in additional detail herein), the inter-element area surface modification may include an analyte-specific probe (e.g., a surface capture ligand) that specifically binds to a magnetically labeled analyte, thereby indirectly binding a specific analyte to the surface of the inter-element area.

In other embodiments, the inter-element area surface modification may be configured to minimize binding of a magnetic label to the inter-element area. For example, the inter-element area surface modification may provide a surface on the inter-element area that minimizes binding interactions between the surface of the inter-element area and magnetic labels. In certain embodiments, the inter-element area surface modification may not include an analyte-specific probe (e.g., a surface capture ligand). Stated another way, the inter-element area surface may be substantially free of an analyte-specific probe (e.g., a surface capture ligand).

In certain embodiments, the inter-element area surface modification includes a chemical modification. In some instances, the inter-element area surface modification includes a layer of a metal. For example, the metal may be gold. In some instances, the metal surface (e.g., gold surface) may be modified to bind to a magnetic label. For example, the metal surface (e.g., gold surface) may be configured to preferentially bind to a magnetic label in a sample being analyzed by the magnetic sensor device. In certain embodiments (and as described in additional detail herein), the metal inter-element area surface modification may include an analyte-specific probe (e.g., a surface capture ligand) that specifically binds to a magnetically labeled analyte, thereby indirectly binding a specific analyte to the metal inter-element area surface modification.

In other embodiments, the metal surface (e.g., gold surface) may be configured to minimize binding of a magnetic label to the inter-element area. For example, the metal surface (e.g., gold surface) may provide a surface on the inter-element area that minimizes binding interactions between the surface of the inter-element area and magnetic labels. In certain embodiments, the metal inter-element area surface modification may not include an analyte-specific probe (e.g., a surface capture ligand). Stated another way, the metal inter-element area surface may be substantially free of an analyte-specific probe (e.g., a surface capture ligand).

As described above, the inter-element area surface modification may include a chemical modification. In certain embodiments, the inter-element area surface modification includes a layer of a dielectric material. For example, the dielectric material may be silicon dioxide. In some instances, the surface of the dielectric material may be modified to bind to a magnetic label. For example, the surface of the dielectric material may be configured to preferentially bind to a magnetic label in a sample being analyzed by the magnetic sensor device. In certain embodiments (and as described in additional detail herein), the dielectric inter-element area surface modification may include an analyte-specific probe (e.g., a surface capture ligand) that specifically binds to a magnetically labeled analyte, thereby indirectly binding a specific analyte to the dielectric inter-element area surface modification.

In other embodiments, the surface of the dielectric material may be configured to minimize binding of a magnetic label to the inter-element area. For example, the surface of the dielectric material may provide a surface on the inter-element area that minimizes binding interactions between the surface of the inter-element area and magnetic labels. In certain embodiments, the dielectric inter-element area surface modification may not include an analyte-specific probe (e.g., a surface capture ligand). Stated another way, the dielectric inter-element area surface may be substantially free of an analyte-specific probe (e.g., a surface capture ligand).

In some embodiments, the inter-element area surface modification includes a layer of the inter-element area surface modification disposed on a surface of the inter-element area. The layer of the inter-element area surface modification may be a substantially contiguous surface layer. By "contiguous" is meant that the inter-element area surface modification covers an area without significant voids or discontinuous areas in the layer of the inter-element area surface modification.

In some cases, the layer of the inter-element area surface modification may be substantially uniform in thickness. For example, the inter-element area surface modification may have a thickness ranging from 1 nm to 1000 nm, such as from 5 nm to 750 nm, or 5 nm to 500 nm, or 10 nm to 250 nm, or 10 nm to 200 nm, or 10 nm to 150 nm, or 15 nm to 150 nm, or 15 nm to 100 nm, or 15 nm to 75 nm, or 15 nm to 50 nm. In some cases, the inter-element area surface modification has a thickness of 15 nm to 150 nm.

In certain embodiments, the sensor surface modification and the inter-element area surface modification include different surface modifications. In certain embodiments, the sensor surface modification may be configured to minimize binding of a magnetic label to the magnetic sensor element, and the inter-element area surface modification may be configured to bind to a magnetic label as described herein (e.g., specific binding to a magnetically labeled analyte through an analyte-specific probe (e.g., a surface capture ligand). In other embodiments, the sensor surface modification may be configured to bind to a magnetic label as described herein (e.g., specific binding to a magnetically labeled analyte through an analyte-specific probe (e.g., a surface capture ligand), and the inter-element area surface modification may be configured to minimize binding of a magnetic label to the magnetic sensor element.

As described above, in certain embodiments, the sensor surface modification and the inter-element area surface modification include different surface modifications. In some embodiments, the sensor surface modification and the inter-element area surface modification include different chemical modifications (e.g., different chemical compositions). For example, as described above, one surface modification may be a metal surface modification and the other surface modification may be a dielectric layer surface modification. In some embodiments, the sensor surface modification includes a layer of a metal on a surface of the magnetic sensor element and the inter-element area surface modification includes a layer of a dielectric material on a surface of the inter-element area. In some cases, the metal is gold and the dielectric material is silicon dioxide. In some embodiments, the sensor surface modification includes a layer of a dielectric material on a surface of the magnetic sensor element and the inter-element area surface modification includes a layer of a metal on a surface of the inter-element area. In certain instances, the dielectric material is silicon dioxide and the metal is gold.

In certain embodiments, the sensor surface modification and the inter-element area surface modification include the same (or substantially the same) surface modification. In some embodiments, the sensor surface modification and the inter-element area surface modification include the same (or substantially the same) chemical modifications (e.g., the same (or substantially the same) chemical compositions). For example, as described above, the surface modifications may be metal surface modifications, or the surface modifications may be dielectric layer surface modifications. In some embodiments, the sensor surface modification and the inter-element area surface modification each include a layer of a metal. In certain instances, the metal is gold. In other embodiments, the sensor surface modification and the inter-element area surface modification each include a layer of a dielectric material. In certain instances, the dielectric material is silicon dioxide.

In certain embodiments, the inter-element area includes a surface modification on a side surface of the magnetic sensor element. The side surface of the magnetic sensor element may be a surface of the magnetic sensor element facing inter-element area, such as facing an interior volume of the inter-element area. As such, the side surface of the magnetic sensor element having a surface modification may be the side of the magnetic sensor element that is adjacent to the inter-element area.

In some embodiments, the inter-element area includes a surface modification on a side surface of the magnetic sensor element that is different from the sensor surface modification and the inter-element area surface modification. In certain embodiments, the sensor surface modification and the inter-element area surface modification may be configured to minimize binding of a magnetic label to the magnetic sensor element, and the side surface modification may be configured to bind to a magnetic label as described herein (e.g., specific binding to a magnetically labeled analyte through an analyte-specific probe (e.g., a surface capture ligand). In other embodiments, the sensor surface modification and the inter-element area surface modification may be configured to bind to a magnetic label as described herein (e.g., specific binding to a magnetically labeled analyte through an analyte-specific probe (e.g., a surface capture ligand), and the side surface modification may be configured to minimize binding of a magnetic label to the magnetic sensor element.

As described herein, in some embodiments, the inter-element area includes a surface modification on a side surface of the magnetic sensor element that is different from the sensor surface modification and the inter-element area surface modification. In some cases, the inter-element area includes a chemical modification (e.g., chemical composition) on a side surface of the magnetic sensor element that is different from the sensor surface chemical modification (e.g., chemical composition) and the inter-element area surface chemical modification (e.g., chemical composition). For example, the sensor surface modification and the inter-element area surface modification may each include a layer of a metal and the side surface modification of the magnetic sensor element may include a layer of a dielectric material. In some embodiments, the metal is gold and the dielectric material is silicon dioxide. In other cases, the sensor surface modification and the inter-element area surface modification may each include a layer of a dielectric material and the side surface modification of the magnetic sensor element may include a layer of a metal. In some embodiments, the dielectric material is silicon dioxide and the metal is gold.

In certain embodiments, the inter-element area includes a surface modification on a side surface of the magnetic sensor element that is the same as the inter-element area surface modification and different from the sensor surface modification. In certain embodiments, the sensor surface modification may be configured to minimize binding of a magnetic label to the magnetic sensor element, and the side surface modification and inter-element area surface modification may be configured to bind to a magnetic label as described herein (e.g., specific binding to a magnetically labeled analyte through an analyte-specific probe (e.g., a surface capture ligand). In other embodiments, the sensor surface modification may be configured to bind to a magnetic label as described herein (e.g., specific binding to a magnetically labeled analyte through an analyte-specific probe (e.g., a surface capture ligand), and the side surface modification and the inter-element area surface modification may be configured to minimize binding of a magnetic label to the magnetic sensor element. For example, the inter-element area may include a surface chemical modification (e.g., chemical composition) on a side surface of the magnetic sensor element that is the same as the inter-element area surface chemical modification (e.g., chemical composition) and different from the sensor surface chemical modification (e.g., chemical composition).

In certain embodiments, as described above, the magnetic sensor element and the inter-element area are substantially coplanar. In some cases, the side surface of the magnetic sensor element forms an angle with the surface of the magnetic sensor element. For example, the angle between the side surface of the magnetic sensor element and the surface of the magnetic sensor element may be 90° or more, such as 95° or more, or 100° or more, or 105° or more, or 110° or more, or 115° or more, or 120° or more. In certain cases, the angle between the side surface of the magnetic sensor element and the surface of the magnetic sensor element is 90°. In some cases, the side surface of the magnetic sensor element forms a corresponding angle with the surface of the inter-element area. For example, the angle between the side surface of the magnetic sensor element and the surface of the inter-element area may be 90° or more, such as 95° or more, or 100° or more, or 105° or more, or 110° or more, or 115° or more, or 120° or more. In certain cases, the angle between the side surface of the magnetic sensor element and the surface of the inter-element area is 90°.

In certain embodiments, the side surface modification of the magnetic sensor element has a thickness ranging from 1 nm to 1000 nm, such as from 5 nm to 750 nm, or 5 nm to 500 nm, or 10 nm to 250 nm, or 10 nm to 200 nm, or 10 nm to 150 nm, or 15 nm to 150 nm, or 15 nm to 100 nm, or 15 nm to 75 nm, or 15 nm to 50 nm. In some cases, the side surface modification of the magnetic sensor element has a thickness of 15 nm to 150 nm.

In some embodiments, the sensor surface modification includes a cover on a surface of the magnetic sensor element. For example the cover may be disposed on a surface of the magnetic sensor element. In some instances, the cover is disposed over substantially the entire surface of the magnetic sensor element (e.g., disposed over substantially the entire top surface of the magnetic sensor element). The cover may be configured to minimize and/or prevent magnetic label binding to a surface of the magnetic sensor element. In these embodiments, a minimization of magnetic label binding to the surface of the magnetic sensor element may facilitate an increase in the sensitivity of the magnetic sensor to magnetic labels in the inter-element area. In some embodiments, the cover is disposed over one or more magnetic sensor elements. For example, the cover may be of a sufficient size to be disposed over two or more magnetic sensor elements, or over an array of magnetic sensor elements. As described in more detail below, the inter-element areas adjacent to the magnetic sensor elements may have a surface (e.g., top surface) that is at a depth below the top surfaces of the adjacent magnetic sensor elements. In these embodiments, the cover disposed on the surfaces of the magnetic sensor elements forms a conduit in the inter-element areas. For instance, the conduit may be bounded on the top by the cover, on the bottom by the inter-element area, and on opposing sides by the side surfaces of magnetic sensor elements adjacent to opposing sides of the inter-element area. In certain cases, a sample may be applied to the magnetic sensor through the conduit and may thus contact the inter-element area and side surfaces of the magnetic sensor elements.

In certain embodiments, a width of the inter-element area is less than a width of the magnetic sensor element. For example, the width of the inter-element area may be 0.1 times or more the width of the magnetic sensor element, such as 0.2 times or more, or 0.3 times or more, or 0.4 times or more, or 0.5 times or more, or 0.6 times or more, or 0.7 times or more, or 0.8 times or more, or 0.9 times or more the width of the magnetic sensor element. In certain cases, the width of the inter-element area is 0.5 times or more the width of the magnetic sensor element.

In certain embodiments, a length of the magnetic sensor element is greater than a width of the magnetic sensor element. For example, the length of the magnetic sensor element may be 1.1 times or more a width of the magnetic sensor element, such as 1.2 times or more, or 1.3 times or more, or 1.4 times or more, or 1.5 times or more, or 1.6 times or more, or 1.7 times or more, or 1.8 times or more, or 1.9 times or more, or 2 times or more the width of the magnetic sensor element. In certain cases, the length of the magnetic sensor element is 1.5 times or more a width of the magnetic sensor element.

In certain embodiments, the inter-element area adjacent to the magnetic sensor element may have a surface (e.g., top surface) that is at a depth below the top surface of the adjacent magnetic sensor element. In these embodiments, the inter-element area and the magnetic sensor element may be coplanar, e.g., the inter-element area and the magnetic sensor element may be arranged on a common (planar) surface of a magnetic sensor device support. In some cases, the top surface of the magnetic sensor element may be at a distance above the surface of the magnetic sensor device support that is greater than the distance above the surface the inter-element area extends. Stated another way, the height of the inter-element area may be less than the height of an adjacent magnetic sensor element. Thus, as measured from the top surface of the magnetic sensor element, the inter-element area may have a depth below the top surface of the magnetic sensor element of 5 nm or more, such as 10 nm or more, or 15 nm or more, or 20 nm or more, or 25 nm or more, or 30 nm, or more, or 35 nm or more, or 40 nm or more, or 45 nm or more, or 50 nm or more, or 55 nm or more, or 60 nm or more, or 65 nm or more, or 70 nm or more, or 75 nm or more, or 80 nm or more, or 85 nm or more, or 90 nm or more, or 95 nm or more, or 100 nm or more. In certain cases, the inter-element area has a depth below the top surface of the magnetic sensor element of 25 nm or more.

In certain embodiments, the magnetic sensor element width and inter-element area width is 10 µm or less, such as 9 µm or less, or 8 µm or less, or 7 µm or less, or 6 µm or less, or 5 µm or less, or 4 µm or less, or 3 µm or less, or 2 µm or less, or 1 µm or less. In certain cases, the magnetic sensor element width and inter-element area width is 2 µm or less.

In certain embodiments, the magnetic sensor element includes a reference layer with a magnetization substantially parallel to a width of the magnetic sensor element. For example, the width dimension of the magnetic sensor element may be disposed along an axis, and the magnetic sensor element includes a reference layer with a magnetization substantially parallel to the axis. By "substantially parallel" is meant that the magnetization of the reference layer is aligned at 25° or less to the axis, such as 20° or less, or 15° or less, or 10° or less, or 5° or less, or 4° or less, or 3° or less, or 2° or less, or 1° or less to the axis (e.g., to the width dimension of the magnetic sensor element). In certain cases, the magnetization of the reference layer is aligned at 10° or less to the axis (e.g., to the width dimension of the magnetic sensor element).

FIG. 1 shows a cross-sectional drawing of a magnetic sensor according to embodiments of the present disclosure. As shown in FIG. 1, a magnetic sensor includes a magnetic sensor element, such as a giant magnetoresistive (GMR) element (also referred to herein as a GMR film), on a support, such as a support composed of a dielectric material (also referred to herein as a dielectric layer (DL), which may be composed of an oxide such as silicon dioxide. The magnetic sensor element (GMR film) has a sensor width (SW) and a sensor length (SL). The magnetic sensor element (GMR film) includes a sensor surface modification (SSM) on a surface of the magnetic sensor element. Adjacent to the magnetic sensor element along the sensor length (SL) is an inter-element area (also referred to herein as a trench). The inter-element area (trench) has an inter-element area width (trench width (TW)) and an inter-element area depth (trench depth (TD)). The inter-element area has an inter-element area length (trench length) that is substantially the same as the sensor length (SL). The inter-element area is adjacent to the magnetic sensor element along the side (also referred to herein as the sensor edge (SE)) of the magnetic sensor element. The side of the magnetic sensor element (sensor edge (SE)) may have a side surface modification as described herein, such as a layer of a dielectric material (or a metal). The side surface modification has a thickness (TH). The inter-element area includes an inter-element area surface modification as described herein (also referred to herein as a trench surface modification (TSM)). As shown in FIG. 1, more than one magnetic sensor may be arranged in series to form an array of magnetic sensors.

Figure 4:
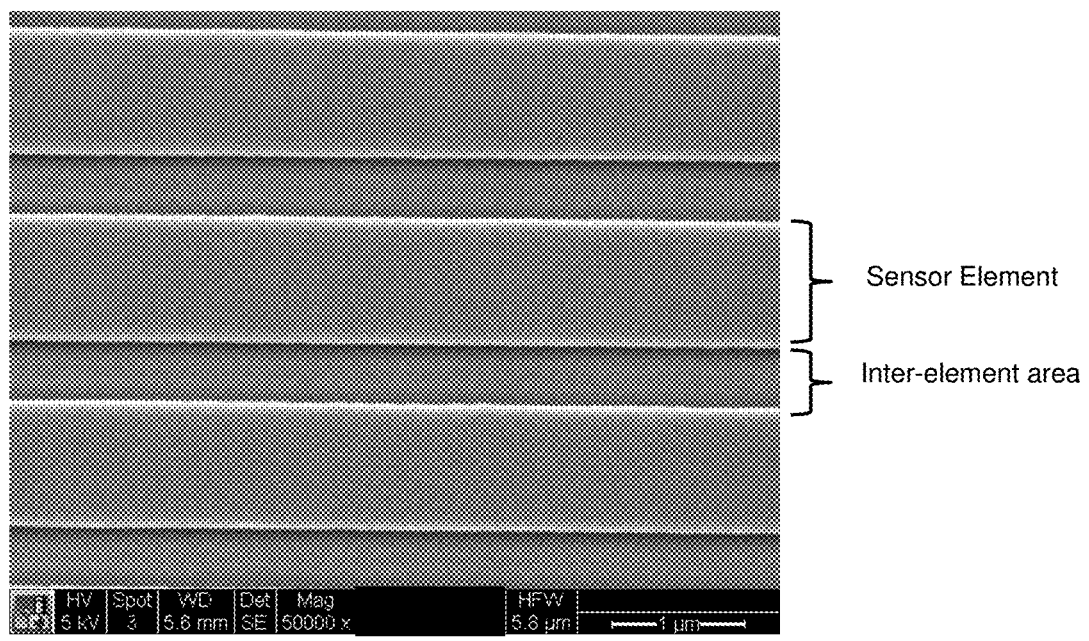
FIG. 4 shows an SEM image of an enlargement of an arrangement of magnetic sensor elements and inter-element areas according to embodiments of the present disclosure.

FIG. 4 shows an SEM image of an enlargement of an arrangement of magnetic sensor elements and inter-element areas according to embodiments of the present disclosure.

Magnetic Sensor Devices

Aspects of the present disclosure include magnetic sensor devices. The magnetic sensor device includes a support. In some embodiments, the support includes an array of magnetic sensors (e.g., an array of biosensors) disposed thereon. In certain embodiments, each magnetic sensor includes one or more magnetic sensor elements as described herein, and one or more inter-element areas as described herein. Aspects of the magnetic sensors are described further in the following sections.

In certain embodiments, a magnetic sensor includes two or more magnetic sensor elements. In some cases, the magnetic sensor elements are electrically connected to each other. In certain cases, the magnetic sensor elements are electrically connected to each other in series. For example, the magnetic sensor elements may be electrically connected to each other in series by one or more electrodes. In some embodiments, by electrically connecting the magnetic sensor elements together in series, a current (e.g., a sense current) may flow through the magnetic sensor elements in series (e.g., sequentially).

Figure 2:
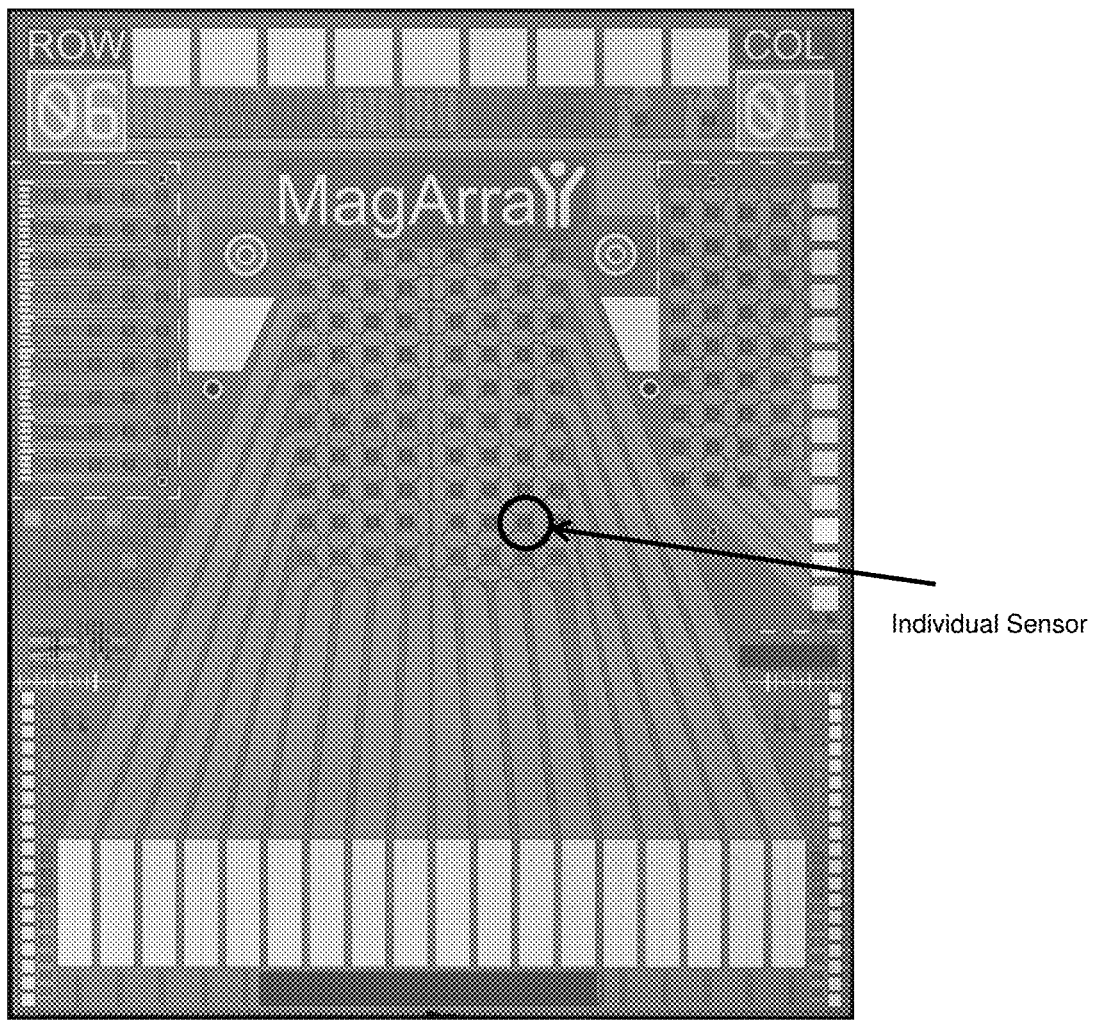
FIG. 2 shows an image of an array of 80 magnetic sensors according to embodiments of the present disclosure.
Figure 3:
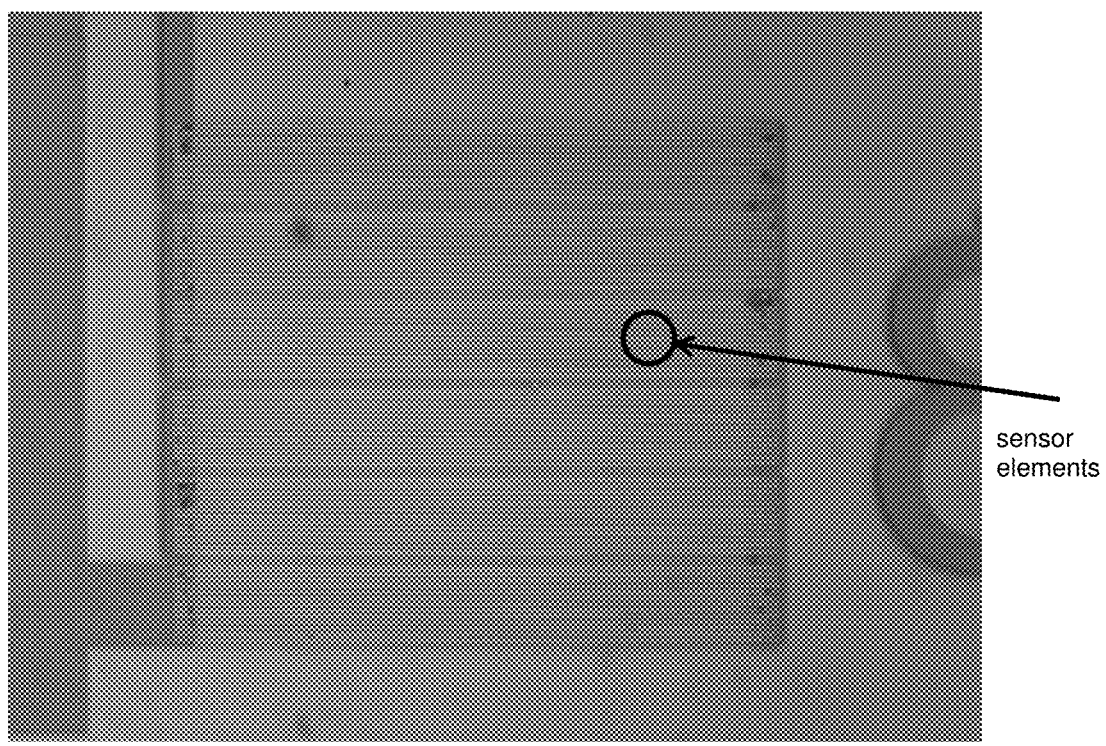
FIG. 3 shows an image of an enlargement of a magnetic sensor of FIG. 2, which shows a plurality of magnetic sensor elements arranged in series and in parallel according to embodiments of the present disclosure.

In certain embodiments, an array of magnetic sensor elements includes a plurality of magnetic sensor elements arranged in series and/or in parallel, which may include two or more magnetic sensor elements, including 3 or more, 4 or more, 6 or more, 8 or more, 10 or more, 15 or more, 20 or more, 25 or more, 30 or more, 40 or more, 50 or more, 75 or more, 100 or more, 125 or more, 150 or more, 175 or more, 200 or more, 225 or more, or 250 or more magnetic sensors arranged in series and/or in parallel. In some cases, the array of magnetic sensor elements includes 100 or more magnetic sensor elements arranged in series and/or in parallel. FIG. 3 shows an enlargement of a magnetic sensor of FIG. 2, which shows a plurality of magnetic sensor elements arranged in series and in parallel according to embodiments of the present disclosure.

In some instances, the magnetic sensor elements are arranged (e.g., arranged in series and/or in parallel as described above) such that the distance between adjacent magnetic sensor elements is 50 μm or less, such as 40 μm or less, including 30 μm or less, or 20 μm or less, or 10 μm or less, or 5 μm or less, or 4 μm or less, or 3 μm or less, or 2 μm or less, or 1 μm or less. In some cases, the distance between adjacent magnetic sensor elements is 2 μm.

In certain embodiments, a magnetic sensor element may have dimensions in the range of 2 μm×2 μm to 200 μm×200 μm, including dimensions of 2 μm×200 μm or less, such as 100 μm×2 μm or less, for instance 2 μm×100 μm or less, or 100 μm×100 μm or less, or 10 μm×10 μm or less, or 5 μm×5 μm or less, or 3 μm×3 μm or less, or 2 μm×2 μm or less, or 1 μm×1 μm or less.

In some instances, an inter-element area has dimensions in the range of 1 μm×1 μm to 100 μm×100 μm, including dimensions of 1 μm×100 μm or less, such as 50 μm×1 μm or less, for instance 1 μm×50 μm or less, or 50 μm×50 μm or less, or 5 μm×5 μm or less, or 4 μm×4 μm or less, or 3 μm×3 μm or less, or 2 μm×2 μm or less, or 1 μm×1 μm or less.

In certain embodiments, an electrode is composed of an electrically conductive material. In some cases, the electrode is made of a conductive metal, e.g., copper, aluminum, palladium, a palladium alloy, a palladium oxide, platinum, a platinum alloy, a platinum oxide, ruthenium, a ruthenium alloy, a ruthenium oxide, silver, a silver alloy, a silver oxide, tin, a tin alloy, a tin oxide, titanium, a titanium alloy, a titanium oxide, tantalum, a tantalum alloy, a tantalum oxide, combinations thereof, and the like. In some instances, the electrode is made of tantalum. In some instances, the electrode is made of ruthenium. In some instances, the electrode includes a layer of an electrically conductive material as described above. For example, the electrode may include a layer of a conductive metal, such as tantalum. In some instances, the electrode includes two or more layers of electrically conductive materials as described above. For example, the electrode may include alternating layers of two different conductive metals, such as tantalum and ruthenium.

In certain embodiments, a magnetic sensor includes a plurality of magnetic sensor elements. In some cases, the magnetic sensor includes two or more magnetic sensor elements (e.g., two or more magnetic sensor elements arranged in series), as described above. In some instances, the magnetic sensor device includes magnetic sensor elements arranged in series and additional magnetic sensor elements electrically connected in parallel to the first series of magnetic sensor arrays. The additional magnetic sensor elements may include two or more magnetic sensor elements arranged in series as described above. As such, in certain cases, the magnetic sensor may include an arrangement of magnetic sensor elements where a plurality of magnetic sensor elements are electrically connected both in series and in parallel.

Aspects of the present disclosure include a magnetic sensor device, where the magnetic sensor device includes a support. In some embodiments, the support includes an array of magnetic sensors (e.g., an array of biosensors) disposed thereon. In certain embodiments, the support has a thickness of 5 mm or less, such as 2 mm or less, including 1.6 mm or less, or 1.0 mm or less, or 0.5 mm or less, or 0.3 mm or less, or 0.2 mm or less. In certain embodiments, the support has a width of 20 mm or less, or 15 mm or less, such as 12 mm or less, including 10 mm or less, or 5 mm or less, or 2 mm or less.

In certain embodiments, the support of the magnetic sensor device is shaped as a rectangular solid (although other shapes are possible), having a length ranging from 1 mm to 20 mm, such as 1 mm to 10 mm, including 1 mm to 5 mm; a width ranging from 1 mm to 20 mm, such as 1 mm to 10 mm, including 1 mm to 5 mm, or 1 mm to 3 mm; and a thickness ranging from 0.1 mm to 5 mm, such as 0.2 mm to 1 mm, including 0.3 mm to 0.5 mm.

Magnetic Sensor Arrays

In certain embodiments, the magnetic sensor device includes an array of magnetic sensors (e.g., an array of biosensors). The array of magnetic sensors may have a variety of different configurations, e.g., with respect to magnetic sensor configuration. In certain embodiments, the subject magnetic sensors are arranged on a biochip (e.g., a biosensor chip). By "biochip" or "biosensor chip" is meant a magnetic sensor device that includes an array of magnetic sensors (e.g., an array of biosensors). For instance, a biochip may include a magnetic sensor device that includes a support surface which displays two or more distinct arrays of magnetic sensors on the support surface. In certain embodiments, the magnetic sensor device includes a support surface with an array of magnetic sensors.

An "array" includes any two-dimensional or substantially two-dimensional (as well as a three-dimensional) arrangement of addressable regions, e.g., spatially addressable regions. An array is "addressable" when it has multiple sensors positioned at particular predetermined locations (e.g., "addresses") on the array. Array features (e.g., sensors) may be separated by intervening spaces. Any given support may carry one, two, four or more arrays disposed on a front surface of the support. Depending upon the use, any or all of the arrays may be the same or different from one another and each may contain multiple distinct magnetic sensors. An array may contain one or more, including 2 or more, 4 or more, 8 or more, 10 or more, 50 or more, 100 or more, 250 or more, 500 or more, 750 or more, 1000 or more magnetic sensors. For example, 64 magnetic sensors can be arranged into an 8×8 array, or 80 magnetic sensors can be arranged in an 8×10 array, or 90 sensors can be arranged in a 9×10 array. FIG. 2 shows an image of an array of 80 magnetic sensors according to embodiments of the present disclosure.

In some instances, the magnetic sensors are arranged in the array in rows and columns of magnetic sensors. For example, an array may include one or more rows of two or more magnetic sensors. In some cases, an array includes 1 or more rows, such as 2 or more, or 3 or more, or 4 or more, or 5 or more, or 6 or more, or 7 or more, or 8 or more, or 9 or more, or 10 or more, or 12 or more, or 14 or more, or 16 or more, or 18 or more, or 20 or more, or 25 or more, or 30 or more, or 35 or more, or 40 or more, or 45 or more, or 50 or more rows of magnetic sensors. In some cases, an array includes 1 or more columns, such as 2 or more, or 3 or more, or 4 or more, or 5 or more, or 6 or more, or 7 or more, or 8 or more, or 9 or more, or 10 or more, or 12 or more, or 14 or more, or 16 or more, or 18 or more, or 20 or more, or 25 or more, or 30 or more, or 35 or more, or 40 or more, or 45 or more, or 50 or more columns of magnetic sensors. For example, 64 magnetic sensors can be arranged into an 8×8 array that includes 8 rows and 8 columns of magnetic sensors, or 80 magnetic sensors can be arranged in an 8×10 array that includes 10 rows and 8 columns of magnetic sensors.

In certain embodiments, the magnetic sensors can be arranged into an array with an area of 10 $cm^2$ or less, or 9 $cm^2$ or less, 5 $cm^2$ or less, 4 $cm^2$ or less, e.g., 2 $cm^2$ or less, 1.2 $cm^2$ or less, 0.1 $cm^2$ or less, including 50 $mm^2$ or less, 20 $mm^2$ or less, such as 10 $mm^2$ or less, or even smaller. For example, the magnetic sensors can be arranged into an array with an area of 15 $mm^2$ or less, such as 12.2 $mm^2$ or less (e.g., 3.2 mm×3.8 mm). In some instances, the magnetic sensors are arranged into an array with an area of 20 $mm^2$. For instance, the magnetic sensors may have a density in an array of 1 magnetic sensor per 2 $mm^2$ array area or less, such as 1 magnetic sensor per 1 $mm^2$ array area or less, or 1 magnetic sensor per 0.5 $mm^2$ array area, or 1 magnetic sensor per 0.2 $mm^2$ array area, or 1 magnetic sensor per 0.16 $mm^2$ array area, or 1 magnetic sensor per 0.14 $mm^2$ array area, or 1 magnetic sensor per 0.12 $mm^2$ array area, or 1 magnetic sensor per 0.1 $mm^2$ array area, or 1 magnetic sensor per 0.08 $mm^2$ array area, or 1 magnetic sensor per 0.05 $mm^2$ array area. In some cases, the magnetic sensors may have a density in an array of 1 magnetic sensor per 0.16 $mm^2$ array area.

In some embodiments, magnetic biosensors with multiple magnetic sensor elements, according to the embodiments of the present disclosure, are dimensioned to cover a portion of the support which is contacted with a sample of biological molecules during an assay. The placement of the sample (e.g., biological molecules) onto individual sensors or inter-element areas may be performed by placing small droplets of a liquid sample with biological molecules onto certain regions of the support, or by placing a stamp coated with biological molecules into contact with the support. In some embodiments, the area of the support coated by a sample of biological molecules and the area of a biosensor are substantially similar. For example, the biosensor may have dimensions in the range of 10 μm×10 μm to 1000 μm×1000 μm, including dimensions of 10 μm×1000 μm or less, such as 1000 μm×10 μm or less, for instance 800 μm×800 μm or less, or 400 μm×400 μm or less, or 200 μm×200 μm or less, or 180 μm×180 μm or less, or 160 μm×160 μm or less, or 140 μm×140 μm or less, or 120 μm×120 μm or less, or 100 μm×100 μm or less, or 80 μm×80 μm or less, or 50 μm×50 μm or less, or 30 μm×30 μm or less. In some instances, a biosensor has dimensions of 140 μm×140 μm or less, such as 120 μm×120 μm.

In some embodiments, magnetic biosensors with multiple magnetic sensor elements, according to the embodiments of the present disclosure, are spaced apart such that the number of biosensors per unit area is maximized, while still allowing individual biosensors to be contacted with separate droplets of a liquid sample containing biological molecules. To achieve substantial separation between adjacent droplets of liquid placed onto individual biosensors, the biosensors may be spaced a certain distance apart and separated by the inter-element areas as described herein.

In certain embodiments, at least some, or all, of the magnetic sensors have an analyte-specific probe (e.g., a surface capture ligand) stably associated with a surface of the sensor or a surface or the inter-element area. For example, each magnetic sensor array may include one or more magnetic sensors having an analyte-specific probe bound to a surface of the magnetic sensor or the inter-element area. Where a given array includes two or more magnetic sensors, each sensor or inter-element area may have the same or different analyte-specific probe associated with its surface. For example, a magnetic sensor array may include two or more distinct magnetic sensors or inter-element areas each configured to specifically detect the same analyte. In some cases, different analyte-specific probes may be present on the sensor surfaces or the inter-element area surfaces of such devices, such that each different analyte-specific probe specifically binds to a distinct analyte. For instance, a magnetic sensor array may include two or more distinct magnetic sensors or distinct inter-element areas each configured to specifically detect a different analyte. In other cases, the magnetic sensor devices include magnetic sensors or inter-element areas that are free of any analyte-specific probes, such that the surface of the magnetic sensor or inter-element area is functionalized to bind directly to the analyte. In some instances, the magnetic sensor or inter-element area includes a blocking layer disposed over the surface of the magnetic sensor or inter-element area. The blocking layer may be configured to inhibit the binding of any analyte-specific probes or analyte to the surface of the magnetic sensor (e.g., where such blocked magnetic sensors may serve as sources of reference or control electrical signals) or inter-element area (e.g., where such blocked inter-element areas may serve as sources of reference or control electrical signals).

As described above, in certain embodiments, the magnetic sensor device includes two or more magnetic sensor arrays disposed on a support. As such, the magnetic sensor device includes two or more magnetic sensor arrays. As described above, each magnetic sensor array may have one or more magnetic sensors or inter-element areas with each magnetic sensor or inter-element area configured to detect the same or different analytes. Thus, each magnetic sensor array on the magnetic sensor device may be configured to detect the same set or different sets of analytes. For example, a magnetic sensor device may include two or more distinct magnetic sensor arrays each configured to specifically detect the same set of analytes. In other cases, a magnetic sensor device may include two or more distinct magnetic sensor arrays each configured to specifically detect a different set of analytes.

Electronic communication elements, e.g., conductive leads, may be present which are configured to electronically couple the magnetic sensors to components of the system, such as processors, displays, etc. Additionally, a given magnetic sensor device may include a variety of other components in addition to the magnetic sensor array. Additional magnetic sensor device components may include, but are not limited to: signal processing components, power sources, fluid handling components, wired or wireless communication components, etc.

In certain embodiments, the magnetic sensor device is configured to produce a detectable signal from a minimum amount of sample. In some instances, the magnetic sensor device is configured to produce a detectable signal from a sample size of 10 mL or less, or 5 mL or less, or 3 mL or less, or 1 mL or less, such as 500 µL or less, including 100 µL or less, for example 50 µL or less, or 25 µL or less, or 10 µL or less. As such, in some cases, the inter-element areas may be configured to receive a minimum amount of sample needed to produce a detectable signal. For example, the inter-element areas may be configured to receive a sample of 10 mL or less, or 5 mL or less, or 3 mL or less, or 1 mL or less, such as 500 µL or less, including 100 µL or less, for example 50 µL or less, or 25 µL or less, or 10 µL or less, or 5 µL or less, or 1 µL or less.

In some embodiments, the magnetic sensor device is configured to connect to a system for detecting the presence of an analyte in a sample. Accordingly, in certain embodiments, the magnetic sensor device does not include a magnetic field source. The magnetic field source may be included in the system for detecting the presence of an analyte in the sample and, thus not included in the magnetic sensor device itself. Thus, the assay protocol may include operably coupling the magnetic sensor device to the system for detecting the presence of an analyte in the sample. In some instances, the magnetic sensor device may be operably coupled to an activation and signal processing unit of the system, as described herein. The magnetic sensor device may include one or more electrical contacts configured to electrically connect the magnetic sensor device to the system, such as to the activation and signal processing unit of the system. The electrical contacts may be arranged along an edge of the magnetic sensor device.

In certain embodiments, the magnetic sensor device includes a programmable memory. In some cases, the programmable memory is configured to store information, such as information including, but not limited to: calibration data (e.g., calibration data for each magnetic sensor and/or each magnetic sensor array); a record of how the magnetic sensors have been prepared with surface functionalization molecules prior to the assay; a record of completed assay steps; a record about which sample was measured; a record of the measurement results; and the like. In some instances, a barcode may be used instead of, or in addition to, the programmable memory. In embodiments of the magnetic sensor device that include a barcode, information associated with the magnetic sensor device may be stored and retrieved from an information system separate from the magnetic sensor device, such as the activation and signal processing unit of the system.

Magnetic Sensors

As described above, each magnetic sensor may include one or more magnetic sensor elements. In some cases, magnetic sensors are sensors configured to detect the presence of nearby magnetic labels without any direct physical contact between the magnetic sensor and the magnetic label. In certain embodiments, the magnetic sensors are configured to detect the presence of an analyte in a sample. For example, a magnetic label may be bound, either directly or indirectly, to an analyte, which in turn may be bound, either directly or indirectly, to the magnetic sensor. If the bound magnetic label is positioned within the detection range of the magnetic sensor, then the magnetic sensor may provide a signal indicating the presence of the bound magnetic label, and thus indicating the presence of the analyte.

In some instances, the magnetic sensors have a detection range from 1 nm to 1000 nm from the surface of the magnetic sensor, such as from 1 nm to 800 nm, including from 1 nm to 500 nm, such as from 1 nm to 300 nm, including from 1 nm to 100 nm from the surface of the magnetic sensor. In some instances, a minimization of the detection range of the sensors may facilitate detection of specifically bound analytes while minimizing detectable signals from analytes not of interest. By "detection range" is meant the distance from the surface of the magnetic sensor where the presence of a magnetic label will induce a detectable signal in the magnetic sensor. In some cases, magnetic labels positioned close enough to the surface of the magnetic sensor to be within the detection range of the magnetic sensor will induce a detectable signal in the magnetic sensor. In certain instances, magnetic labels positioned at a distance from the surface of the magnetic sensor that is greater than the detection range of the magnetic sensor will not induce a detectable or non-negligible signal in the magnetic sensor. For example, a magnetic label may have a magnetic flux that is proportional to $1/r^3$, where r is the distance between the magnetic sensor and the magnetic label. Thus, only those magnetic labels that are positioned in close proximity (e.g., within the detection range of the magnetic sensor) will induce a detectable signal in the magnetic sensor.

In certain embodiments, the surface of the magnetic sensor is functionalized to bind directly to an analyte or a magnetic label. For example, the surface of the magnetic sensor may be functionalized to provide for covalent binding or non-covalent association between the analyte or the magnetic label and magnetic sensor, including, but not limited to, non-specific adsorption, binding based on electrostatic interactions (e.g., ion-ion pair interactions), hydrophobic interactions, hydrogen bonding interactions, and the like.

In some instances, the surface of the magnetic sensor or the inter-element area includes an analyte-specific probe (e.g., a surface capture ligand) that specifically binds to an analyte. The analyte-specific probe may be bound to the surface of the magnetic sensor or the inter-element area. For instance, a cationic polymer such as polyethyleneimine (PEI) can be used to nonspecifically bind charged antibodies to the surface via physiabsorption. Alternatively, a covalent chemistry can be used utilizing free amines or free thiol groups on the analyte-specific probe to covalently bind the analyte-specific probe to the surface of the magnetic sensor or the inter-element area. For example, an N-hydroxysuccinimide (NHS) to 1-ethyl-3-(3-dimethylaminopropyl) carbodiimide (EDC) coupling system may be used to covalently bind the analyte-specific probe to the surface of the magnetic sensor or the inter-element area.

The analyte-specific probe may include one member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like. In certain embodiments, the surface of the magnetic sensor or the inter-element area includes an antibody that specifically binds to an analyte of interest. Accordingly, contacting the magnetic sensor or the inter-element area with an assay composition that includes the analyte of interest may result in binding of the analyte to the analyte-specific probe (e.g., antibody) bound to the surface of the magnetic sensor or the inter-element area.

In certain embodiments, the magnetic sensor is configured to generate an electrical signal in response to a magnetic label in proximity to a surface of the magnetic sensor. For example, the magnetic sensors may be configured to detect changes in the resistance of the magnetic sensor induced by changes in the local magnetic field. In some cases, binding of a magnetic label (e.g., a magnetic nanoparticle label) in close proximity to the magnetic sensor, as described above, induces a detectable change in the resistance of the magnetic sensor. For instance, in the presence of an applied external magnetic field, the magnetic labels near the magnetic sensor may be magnetized. The local magnetic field of the magnetized magnetic labels may induce a detectable change in the resistance of the underlying magnetic sensor. Thus, the presence of the magnetic labels can be detected by detecting changes in the resistance of the magnetic sensor. In certain embodiments, the magnetic labels near the magnetic sensor may be present in an inter-element area such as bound to an inter-element area as described herein. In certain embodiments, the magnetic labels near the magnetic sensor may be present in an inter-element area such as bound to a side surface of a magnetic sensor element as described herein.

In certain embodiments, the magnetic sensors are configured to detect changes in resistance of 1 Ohm or less, such as 500 mOhm or less, including 100 mOhm or less, or 50 mOhm or less, or 25 mOhm or less, or 10 mOhm or less, or 5 mOhm or less, or 1 mOhm or less. In certain embodiments, the change in resistance may be expressed in parts per million (PPM) relative to the original sensor resistance, such as a change in resistance of 2 PPM or more, or 20 PPM or more, or 200 PPM or more, or 400 PPM or more, or 600 PPM or more, or 1000 PPM or more, or 2000 PPM or more, or 4000 PPM or more, or 6000 PPM or more, or 10,000 PPM or more, or 20,000 PPM or more, or 40,000 PPM or more, or 60,000 PPM or more, or 100,000 PPM or more, or 200,000 PPM or more.

In certain cases, the magnetic sensor is a multilayer thin film structures. The sensors may include alternating layers of a ferromagnetic material and a non-magnetic material. The ferromagnetic material may include, but is not limited to, Permalloy (NiFe), iron cobalt (FeCo), nickel iron cobalt (NiFeCo), nickel oxide (NiO), cobalt oxide (CoO), nickel cobalt oxide (NiCoO), ferric oxide ($Fe_2O_3$), CoFeB, Ru, PtMn, combinations thereof, and the like. In some cases, the non-magnetic material is an insulating layer, such as, but not limited to, MgO, alumina, and the like. In certain embodiments, the ferromagnetic layers have a thickness of 1 nm to 10 nm, such as 2 nm to 8 nm, including 3 nm to 4 nm. In some instances, the non-magnetic layer has a thickness of 0.2 nm to 5 nm, such as 1 nm to 3 nm, including 1.5 nm to 2.5 nm, or 1.8 nm to 2.2 nm.

Spin Valve Magnetoresistive Elements

In certain embodiments, the magnetic sensor element is a spin valve magnetoresistive element. In certain cases, the spin valve element is a multilayer structure that includes a first ferromagnetic layer, a non-magnetic layer disposed on the first ferromagnetic layer, and a second ferromagnetic layer disposed on the non-magnetic layer. The first ferromagnetic layer may be configured to have its magnetization vector fixed in a certain direction. In some cases, the first ferromagnetic layer is called the "pinned layer". In certain embodiments, the spin valve element includes a pinned layer with a magnetization substantially parallel to a width of the magnetic sensor element, as described above. The second ferromagnetic layer may be configured such that its magnetization vector can rotate freely under an applied magnetic field. In some cases, the second ferromagnetic layer is called the "free layer".

In certain instances, the electrical resistance of a spin valve element depends on the relative orientation of the magnetization vector of the free layer to that of the pinned layer. When the two magnetization vectors are parallel, the resistance is the lowest; when the two magnetization vectors are antiparallel, the resistance is the highest. The relative change of resistance is called the magnetoresistance (MR) ratio. In certain embodiments, a spin valve element has a MR ratio of 1% to 20%, such as 3% to 15%, including 5% to 12%. In some cases, the MR ratio of a spin valve element is 10% or more in a small magnetic field, e.g., 100 Oe. Changes in the resistance of the spin valve element due to the presence of magnetic labels near the surface of the spin valve element may be detected, as described above.

In certain embodiments, the signal from the spin valve element due to the magnetic label depends on the distance between the magnetic label and the free layer of the spin valve element. In some cases, the voltage signal from a magnetic label decreases as the distance from the center of the magnetic label to the mid-plane of the free layer increases. Thus, in certain instances, the free layer in the spin valve element is positioned at the surface of the spin valve element. Positioning the free layer at the surface of the spin valve element may minimize the distance between the free layer and any bound magnetic labels, which may facilitate detection of the magnetic labels.

In certain embodiments, the spin valve element may include a passivation layer disposed on one or more of the spin valve element surfaces. In some cases, the passivation layer has a thickness of 60 nm or less, such as 50 nm or less, including 40 nm or less, 30 nm or less, 20 nm or less, 10 nm or less. For instance, the passivation layer may have a thickness of 1 nm to 10 nm, such as from 1 nm to 5 nm, including from 1 nm to 3 nm. In certain embodiments, the passivation layer includes gold, tantalum, $SiO_2$, $Si_3N_4$, combinations thereof, and the like.

Magnetic Tunnel Junction (MTJ) Magnetoresistive Elements

In certain embodiments, the magnetic sensor element is a magnetic tunnel junction (MTJ) magnetoresistive element (also referred to herein as an MTJ element). In some cases, the MTJ element includes a multilayer structure that includes a first ferromagnetic layer, an insulating layer disposed on the first ferromagnetic layer, and a second ferromagnetic layer disposed on the insulating layer. The insulating layer may be a thin insulating tunnel barrier, and may include alumina, MgO, and the like. In some cases, electron tunneling between the first and the second ferromagnetic layers depends on the relative magnetization of the two ferromagnetic layers. For example, in certain embodiments, the tunneling current is high when the magnetization vectors of the first and second ferromagnetic layers are parallel and the tunneling current is low when the magnetization vectors of the first and second ferromagnetic layers antiparallel.

In some instances, a MTJ element has a magnetoresistance ratio (MR) of 1% to 300%, such as 10% to 250%, including 25% to 200%. Changes in the resistance of the MTJ element due to the presence of magnetic labels near the surface of the MTJ element may be detected, as described above. In some instances, the MTJ element has an MR of 50% or more, or 75% or more, or 100% or more, or 125% or more, or 150% or more, or 175% or more, or 200% or more, or 225% or more, or 250% or more, or 275% or more, or 200% or more. For instance, the MTJ element may have an MR of 225% or more.

In certain embodiments, the second ferromagnetic layer (e.g., the layer of the MTJ element positioned at the surface of the MTJ element) includes two of more layers. For example, the second ferromagnetic layer may include a first layer, a second layer disposed on the first layer, and a third layer disposed on the second layer. In some cases, the first layer is a thin ferromagnetic layer (e.g., NiFe, CoFe, CoFeB, and the like). The thin metallic layer may have a thickness of 6 nm or less, such as 5 nm or less, including 4 nm or less, 3 nm or less, 2 nm or less, or 1 nm or less, or 0.5 nm or less. The second layer may include a conductive metal, e.g., copper, aluminum, palladium, a palladium alloy, a palladium oxide, platinum, a platinum alloy, a platinum oxide, ruthenium, a ruthenium alloy, a ruthenium oxide, silver, a silver alloy, a silver oxide, tin, a tin alloy, a tin oxide, titanium, a titanium alloy, a titanium oxide, tantalum, a tantalum alloy, a tantalum oxide, combinations thereof, and the like. The second layer may have a thickness of 2 nm or less, such as 0.5 nm or less, including 0.4 nm or less, 0.3 nm or less, 0.2 nm or less, or 0.1 nm or less. The third layer may include a ferromagnetic material such as, but not limited to, NiFe, CoFe, CoFeB, and the like. The third layer may have a thickness of 6 nm or less, such as 5 nm or less, including 4 nm or less, 3 nm or less, 2 nm or less, or 1 nm or less, or 0.5 nm or less.

In some cases, the MTJ element is configured such that the distance between an associated magnetic label and the top surface of the free layer ranges from 5 nm to 1000 nm, or 10 nm to 800 nm, such as from 20 nm to 600 nm, including from 40 nm to 400 nm, such as from 60 nm to 300 nm, including from 80 nm to 250 nm.

The MTJ element may include a passivation layer disposed on one or more of the MTJ element surfaces. In some instances, the passivation layer has a thickness of 60 nm or less, such as 50 nm or less, including 40 nm or less, 30 nm or less, 20 nm or less, 10 nm or less. For example, the passivation layer may have a thickness of 1 nm to 50 nm, such as from 1 nm to 40 nm, including from 1 nm to 30 nm, or form 1 nm to 20 nm. In some instances, the passivation layer has a thickness of 30 nm. In some cases, the passivation layer includes gold, tantalum, a tantalum alloy, a tantalum oxide, aluminum, an aluminum alloy, an aluminum oxide, $SiO_2$, $Si_3N_4$, $ZrO_2$, combinations thereof, and the like. In certain embodiments, a passivation layer with a thickness as described above facilitates a maximization in signal detected from magnetic labels specifically bound to the sensor surface or the inter-element area while minimizing the signal from magnetic labels that are not specifically bound.

In certain embodiments, a MTJ element has dimensions ranging from 1 µm×1 µm to 200 µm×200 µm, including dimensions of 1 µm×200 µm or less, such as 200 µm×1 µm or less, for instance 150 µm×10 µm or less, or 120 µm×5 µm or less, or 120 µm×0.8 µm or less, or 0.8 µm×120 µm or less, or 100 µm×0.7 µm or less, or 100 µm×0.6 µm or less, or 100 µm×0.5 µm or less, or 10 µm×0.6 µm or less, or 10 µm×0.5 µm or less. In some instances, a MTJ element has dimensions of 120 µm×0.8 µm or less, such as 2.0 µm×0.8 µm.

Magnetic tunnel junction (MTJ) detectors are further described in U.S. Application Publication No. 2009/0104707, filed Sep. 19, 2008, the disclosure of which is hereby incorporated by reference in its entirety. Detectors are further described in U.S. Pat. No. 7,906,345, filed Apr. 22, 2004, the disclosure of which is hereby incorporated by reference in its entirety.

Magnetic Sensing Areas

In certain embodiments, the magnetic sensor device may be configured to include one or more magnetic sensing areas. A magnetic sensing area may correspond to the area of the device where an array of magnetic sensors (e.g., an array of biosensors) is positioned. For instance, the magnetic sensing area may be an area on the surface of the device that is exposed to the sample during use, and which has an array of magnetic sensors (e.g., an array of biosensors) as described above.

The magnetic sensing area may be configured to include a fluid reservoir. The fluid reservoir may be any of a variety of configurations, where the fluid reservoir is configured to hold a sample in contact with the magnetic sensor arrays. Accordingly, configurations of the fluid reservoirs may include, but are not limited to: cylindrical well configurations, square well configurations, rectangular well configurations, round bottom well configurations, and the like. For instance, the fluid reservoirs may include walls that separate one fluid reservoir from adjacent fluid reservoirs. The walls may be substantially vertical with respect to the surface of the reservoir plate. In some cases, the walls of each fluid reservoir define a volume of space that may receive a volume of sample equal to or less than the volume of space defined by the fluid reservoir.

In certain embodiments, a fluid reservoir has a volume of 10 mL or less, or 5 mL or less, or 3 mL or less, or 1 mL or less, such as 500 µL or less, including 100 µL or less, for example 50 µL or less, or 25 µL or less, or 10 µL or less, which is sufficient to contain a sample volume of an equal or lesser volume.

Magnetic Sensor Systems

In certain embodiments, the systems include a magnetic sensor device, and a magnetic field source. The magnetic sensor device includes a support having two or more arrays of magnetic sensors (e.g., arrays of biosensors) positioned thereon. The system may be configured to obtain signals from each array of magnetic sensors indicating whether one or more analytes is present in each sample.

In certain embodiments, the system includes a magnetic field source. The magnetic field source may be configured to apply a magnetic field to the magnetic sensor device (e.g., the magnetic sensor arrays) sufficient to produce a DC and/or AC field in the assay sensing area (e.g. in the area where the magnetic sensor arrays are positioned during signal acquisition). In some instances, the magnetic field source is configured to produce a magnetic field with a magnetic field strength of 1 Oe or more, or 5 Oe or more, or 10 Oe or more, or 20 Oe or more, or 30 Oe or more, or 40 Oe or more, or 50 Oe or more, or 60 Oe or more, or 70 Oe or more, or 80 Oe or more, or 90 Oe or more, or 100 Oe or more.

The magnetic field source may be positioned such that a magnetic field is produced in the area where the magnetic sensor arrays are positioned when the magnetic sensor device is in use. In some cases, the magnetic field source is configured to generate a uniform, controllable magnetic field around the set of fluid reservoirs on the reservoir plate where an assay is being performed. The magnetic field source may include one or more, such as two or more, three or more, four or more magnetic field generating components. In some cases, the magnetic field source may include one or more electromagnets, such as coil electromagnets. The coil electromagnets may include wire-wound coils. For example, the magnetic field source may include two electromagnets arranged in a Helmholtz coil geometry.

Embodiments of the systems further include computer-based systems. The systems may be configured to qualitatively and/or quantitatively assess binding interactions as described above. A "computer-based system" refers to the hardware, software, and data storage components used to analyze the signals from the magnetic sensors. The hardware of the computer-based systems may include a central processing unit (CPU), inputs, outputs, and data storage components. Any of a variety of computer-based systems is suitable for use in the subject systems. The data storage components may include any computer readable medium that includes a device for recording signals from the magnetic sensor arrays, or an accessible memory component that can store signals from the magnetic sensor arrays.

To "record" data, programming or other information on a computer readable medium refers to a process for storing information, using any such methods as known in the art. Any convenient data storage structure may be chosen, depending on the method used to access the stored information. A variety of data processor programs and formats can be used for storage, e.g. word processing text file, database format, etc.

In certain embodiments, the system includes an activation and signal processing unit. The activation and signal processing unit may be configured to operably couple to the magnetic sensor device. In some instances, the activation and signal processing unit is electrically coupled to the magnetic sensor device. The activation and signal processing unit may be electrically coupled such as to provide bi-directional communication to and from the magnetic sensor device. For example, the activation and signal processing unit may be configured to provide power, activation signals, etc. to components of the magnetic sensor device, such as, but not limited to the magnetic sensor arrays. As such, the activation and signal processing unit may include an activation signal generator. The activation signal generator may be configured to provide power, activation signals, etc. to components of the analyte detection device, such as, but not limited to the magnetic sensor arrays. In some instances, the activation and signal processing unit is configured to apply a voltage across the magnetic sensor arrays ranging from 1 mV to 10 V, such as 100 mV to 5 V, including 200 mV to 1 V, for example, 300 mV to 500 mV. In some cases, the activation and signal processing unit is configured to apply a voltage across the magnetic sensor arrays of 500 mV.

Additionally, the activation and signal processing unit may be configured to receive signals from the magnetic sensor device, such as from the magnetic sensor arrays of the magnetic sensor device. The signals from the magnetic sensor arrays of the magnetic sensor device may be used to detect the presence of one or more analytes in the samples. In some instances, the activation and signal processing unit may include a processor configured to output an analyte detection result in response to receiving signals from the magnetic sensor arrays. Thus, the processor of the activation and signal processing unit may be configured to receive signals from the magnetic sensor device, process the signals according to a predetermined algorithm, obtain a result related to the presence of one or more analytes in the samples, and output the result to a user in a human-readable or an audible format.

A "processor" references any hardware and/or software combination that will perform one or more programmed functions. For example, any processor herein may be a programmable digital microprocessor such as available in the form of an electronic controller, mainframe, server or personal computer (e.g., desktop or portable). Where the processor is programmable, suitable programming can be communicated from a remote location to the processor, or previously saved in a computer program product (such as a portable or fixed computer readable storage medium, whether magnetic, optical or solid-state device based). For example, a magnetic medium, optical disk or solid-state memory device may carry the programming, and can be read by a suitable reader communicating with the processor.

In some instances, the subject systems are configured to modulate the current applied to the magnetic sensor arrays (e.g., the sense current). The subject systems may also be configured to modulate the magnetic field generated by the magnetic field source. Modulating the sense current and the magnetic field may facilitate a minimization in signal noise, and thus a maximization in the signal to noise ratio. Additional aspects of modulating the sense current and the magnetic field are described in more detail in U.S. Application Publication No. 2011/0027901, filed on Apr. 13, 2010, the disclosure of which is incorporated herein by reference in its entirety.

Embodiments of the subject systems may also include the following components: (a) a wired or wireless communications module configured to transfer information between the system and one or more users, e.g., via a user computer, as described below; and (b) a processor for performing one or more tasks involved in the qualitative and/or quantitative analysis of the signals from the magnetic sensors. In certain embodiments, a computer program product is provided that includes a computer-usable medium having control logic (e.g., a computer software program, including program code) stored therein. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the magnetic sensor device and activation and signal processing unit, the systems may include a number of additional components, such as, but not limited to: data output devices, e.g., monitors, speakers, etc.; data input devices, e.g., interface ports, buttons, switches, keyboards, etc.; fluid handling components, e.g., microfluidic components; power sources; power amplifiers; wired or wireless communication components; etc. For example, the systems may include fluid handling components, such as microfluidic fluid handling components. In certain embodiments, the microfluidic fluid handling components are configured to deliver a fluid to the inter-element areas. In some cases, the fluid includes one or more of the following: an assay composition, a sample, a magnetic label, a capture probe, a reagent, and the like. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less.

In certain embodiments, the system is a high-sensitivity analyte detector. By "high-sensitivity" is meant that the system is configured to detect an analyte in a sample, where the concentration of the analyte in the sample is low. In some cases, the system is configured to produce a detectable signal indicating the presence of an analyte of interest in a sample where the concentration of the analyte in the sample is 1 µM or less, such as 100 nM or less, or 10 nM or less, or 1 nM or less, including 100 pM or less, or 10 pM or less, or 1 pM or less, for example 500 fM or less, or 250 fM or less, or 100 fM or less, or 50 fM or less, or 25 fM or less, such as 10 fM or less, or 5 fM or less, or 1 fM or less. Stated another way, the system may be configured to have a detection limit, e.g., a lower limit of quantitation (LLOQ), of 1 pM or less, such as 100 nM or less, or 10 nM or less, or 1 nM or less, including 100 pM or less, or 10 pM or less, or 1 pM or less, for example 500 fM or less, or 250 fM or less, or 100 fM or less, or 50 fM or less, or 25 fM or less, such as 10 fM or less, or 5 fM or less, or 1 fM or less.

In certain embodiments, the systems include a display. The display may be configured to provide a visual indication of an analyte detection result obtained from the activation and signal processing unit, as described above. The display may be configured to display a qualitative analyte detection result. For instance, the qualitative display may be configured to display qualitative indicators to a user that a sample includes or does not include a specific analyte of interest. In some embodiments, the display may be configured to display an analyte detection result, where the analyte detection result is a quantitative result, e.g., a quantitative measurement of the concentration of an analyte in a sample. For example, in embodiments where the system is configured to output a quantitative analyte detection result, the system may include a display configured to display the quantitative analyte detection result.

The magnetic sensor device optionally includes a programmable memory, which prior to and during the use of the magnetic sensor device can be programmed with relevant information such as: calibration data for each individual sensor; a record of how the biochip has been prepared with surface functionalization molecules prior to the assay; a record of all completed assay steps; a record about which sample was measured; a record of the measurement results; and the like.

Methods

Aspects of the present disclosure also include a method for evaluating whether an analyte is present in a sample. The method includes contacting a magnetic sensor device with a sample to generate a signal. In addition, the method includes evaluating whether the analyte is present in each sample based on the signal.

Embodiments of the methods are directed to evaluating whether an analyte is present in a sample, e.g., determining the presence or absence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence of two or more distinct analytes, in which the two or more analytes are different from each other, is determined. For example, analytes may include detectable differences in their molecular structure, sequence, and the like. In some instances, the number of analytes is greater than 2, such as 4 or more, 6 or more, 8 or more, etc., up to 20 or more, e.g., 50 or more, including 100 or more, or 1000 or more distinct analytes. In certain embodiments, the methods include the multiplex analysis of 2 to 1000 distinct analytes, such as 4 to 500 distinct analytes, including 4 to 200 distinct analytes, or 4 to 100 distinct analytes, or 4 to 50 distinct analytes, or 4 to 20 distinct analytes. In certain embodiments, several multiplex assays may be conducted in parallel substantially simultaneously.

In some instances, the methods are wash-free methods of evaluating the presence of one or more analytes in a sample. By "wash-free" is meant that no washing step is performed following reagent and/or sample contact with a magnetic sensor. As such, no step is performed during the assays of these embodiments in which unbound reagent (e.g., unbound magnetic labels) or unbound sample is removed from the magnetic sensor surface. Accordingly, while the methods may include sequential contact of one or more distinct reagents and/or samples to a magnetic sensor surface, at no point during the assay is the sample surface contacted with a fluid in a manner that removes unbound reagent or sample from the magnetic sensor surface. For example, in certain embodiments, no washing step is performed following contact of the magnetic sensor surface with a sample. In some cases, the method does not include a washing step following contact of the magnetic sensor surface with a magnetic label. In certain instances, no washing step is performed following contact of the magnetic sensor surface with a capture probe.

In certain embodiments where a wash step is performed, the wash step does not substantially change the signal from the magnetic sensor. The wash step may not result in a substantial change in the signal from the magnetic sensor because, in some instances, unbound magnetic labels do not have a substantially detectable signal as described herein. For example, if a wash step is performed, in some cases, the wash step results in a signal change of 25% or less, such as 20% or less, or 15% or less, or 10% or less or 5% or less, or 4% or less, or 3% or less, or 2% or less, or 1% or less. In some embodiments, the wash step results in a decrease in the signal from the magnetic sensor of 25% or less, such as 20% or less, or 15% or less, or 10% or less or 5% or less, or 4% or less, or 3% or less, or 2% or less, or 1% or less.

Aspects of the methods may also include obtaining a real-time signal from the magnetic sensor device. As such, embodiments of the method include obtaining a real-time signal from the magnetic sensor arrays. By "real-time" is meant that a signal is observed as it is being produced or immediately thereafter. For example, a real-time signal is obtained from the moment of its initiation and is obtained continuously over a given period of time. Accordingly, certain embodiments include observing the evolution in real time of the signal associated with the occurrence of a binding interaction of interest (e.g., the binding of the analyte of interest to the magnetic sensor or the inter-element area and/or binding of a magnetic label to the analyte of interest). The real-time signal may include two or more data points obtained over a given period of time, where in certain embodiments the signal obtained is a continuous set of data points (e.g., in the form of a trace) obtained continuously over a given period of time of interest. The time period of interest may vary, ranging in some instances from 0.5 min to 60 min, such as 1 min to 30 min, including 1 min to 15 min, or 1 min to 10 min. For example, the time period may begin at the moment of initiation of the real-time signal and may continue until the magnetic sensor reaches a maximum or saturation level (e.g., where all the analyte binding sites on the magnetic sensor are occupied). For example, in some cases, the time period begins when a sample is contacted with the magnetic sensor. In some cases, the time period may begin prior to contacting the sample with the magnetic sensor, e.g., to record a baseline signal before contacting sample to the magnetic sensor. The number of data points in the signal may also vary, where in some instances, the number of data points is sufficient to provide a continuous stretch of data over the time course of the real-time signal. By "continuous" is meant that data points are obtained repeatedly with a repetition rate of 1 data point per minute or more, such as 2 data points per minute or more, including 5 data points per minute or more, or 10 data points per minute or more, or 30 data points per minute or more, or 60 data points per minute or more (e.g., 1 data point per second or more), or 2 data points per second or more, or 5 data points per second or more, or 10 data points per second or more, or 20 data points per second or more, or 50 data points per second or more, or 75 data points per second or more, or 100 data points per second or more.

In certain embodiments, the real-time signal is a real-time analyte-specific signal. A real-time analyte-specific signal is a real-time signal as described above that is obtained only from the specific analyte of interest. In these embodiments, unbound analytes and unbound magnetic labels do not produce a detectable signal. In these embodiments, non-specifically bound analytes and non-specifically bound magnetic labels do not produce a detectable signal. As such, the real-time signal that is obtained is only from the specific magnetically-labeled analyte of interest bound to the magnetic sensor or inter-element area and substantially no signal is obtained from unbound or non-specifically bound magnetic labels or other reagents (e.g., analytes not specifically bound to the sensor).

In some embodiments, the signal is observed while the assay device is in a wet condition. By "wet" or "wet condition" is meant that the assay composition (e.g., an assay composition that includes a sample, a magnetic label, and a capture probe) is still in contact with the surface of the magnetic sensor. As such, there is no need to perform any washing steps to remove the non-binding moieties that are not of interest or the excess unbound magnetic labels or capture probes. In certain embodiments, the use of magnetic labels and magnetic sensors, as described above, facilitates "wet" detection because the signal induced in the magnetic sensor by the magnetic label decreases as the distance between the magnetic label and the surface of the magnetic sensor increases. For example, the use of magnetic labels and magnetic sensors, as described above, may facilitate "wet" detection because the magnetic field generated by the magnetic labels decreases as the distance between the magnetic label and the surface of the magnetic sensor increases. In some instances, the magnetic field of the magnetic label bound to the surface-bound analyte significantly exceeds the magnetic field from the unbound magnetic labels dispersed in solution. For example, as described above, a real-time analyte-specific signal may be obtained only from the specific magnetically-labeled analyte of interest bound to the magnetic sensor and substantially no signal may be obtained from unbound magnetic labels dispersed in solution (e.g., not specifically bound to the sensor). The unbound magnetic labels dispersed in solution may be at a greater distance from the surface of the magnetic sensor and may be in Brownian motion, which may reduce the ability of the unbound magnetic labels to induce a detectable change in the resistance of the magnetic sensor.

Assay Protocol

A typical assay protocol, as well as the individual components of the assay, is described in the following sections.

In certain embodiments, the method includes contacting a magnetic sensor array with an assay composition that includes a sample. The magnetic sensor array may then be contacted with a magnetic label and a capture probe configured to bind to the magnetic label. A signal is obtained from the sensor to detect the presence of the analyte in the sample. Each of these steps will now be described in greater detail.

Sample

As described above, assay compositions that may be assayed in the subject methods include a sample. Samples that may be assayed in the subject methods may vary, and include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analytes of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure.

In certain embodiments, the samples of interest are biological samples, such as, but not limited to, urine, blood, serum, plasma, saliva, perspiration, feces, cheek swabs, cerebrospinal fluid, cell lysate samples, and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In some instances, the samples of interest are water, food or soil samples.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

Magnetic Labels

Assay compositions that may be assayed in the subject methods include a magnetic label. Magnetic labels are labeling moieties that are detectable by a sensor, such as a magnetic sensor, when the magnetic label is positioned near the magnetic sensor. While the distance between the magnetic label and magnetic sensor during detection may vary depending on the nature of the specific magnetic label and magnetic sensor, in some instances this distance ranges from 1 nm to 1000 nm from the magnetic sensor, or 1 nm to 800 nm from the magnetic sensor, such as from 5 nm to 500 nm, including from 5 nm to 100 nm. In certain embodiments, the magnetic labels are detectable labels that are configured to specifically bind to an analyte of interest. The terms "specific binding," "specifically bind," and the like, refer to the ability of a first binding molecule or moiety (e.g., a target-specific binding moiety) to preferentially bind directly to a second binding molecule or moiety (e.g., a target molecule) relative to other molecules or moieties in a solution or assay mixture. In certain embodiments, the affinity between a first binding molecule or moiety and a second binding molecule or moiety when they are specifically bound to each other in a binding complex is characterized by a $K_D$ (dissociation constant) of less than $10^{-6}$ M, less than $10^{-7}$ M, less than $10^{-8}$ M, less than $10^{-8}$ M, less than $10^{-10}$ M, less than $10^{-11}$ M, less than $10^{-12}$ M, less than $10^{-13}$ M, less than $10^{-14}$ M, or less than $10^{-16}$ M.

Binding of the magnetic label to the analyte of interest allows the analyte of interest to be detected by a magnetic sensor when the analyte of interest, and thus the bound magnetic label, is positioned near the magnetic sensor. In some cases, the magnetic labels are configured to bind directly to an analyte of interest. In other cases, the magnetic labels are configured to indirectly bind to an analyte of interest. For instance, a magnetic label may be configured to specifically bind to a capture probe, and the capture probe may be configured to specifically bind to the analyte of interest. Thus, binding of the magnetic label and the analyte of interest to the capture probe indirectly binds the magnetic label to the analyte of interest, e.g., to produce a labeled analyte. In some instances, the binding of the magnetic label and analyte to the capture probe is simultaneous.

In certain embodiments, the magnetic label is functionalized with one member of a binding pair. By "binding pair" or "specific binding pair" is meant two complementary binding molecules or moieties that specifically bind to each other in a binding complex. For example, a magnetic label may be functionalized with a first member of a binding pair and an analyte of interest may be functionalized with a second member of a binding pair. Thus, contacting the first and second members of the binding pair may form a binding complex between the magnetic label and the analyte of interest. In other cases, a magnetic label is functionalized with a first member of a binding pair and a capture probe is functionalized with a second member of a binding pair. Thus, contacting the first and second members of the binding pair may form a binding complex between the magnetic label and the capture probe. As described above, in some cases, the capture probe is configured to specifically bind to an analyte of interest. As such, the magnetic label may be indirectly bound to the analyte of interest through the binding complex formed between the magnetic label and the capture probe. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like.

In certain embodiments, the magnetic label is functionalized with streptavidin and the capture probe is functionalized with biotin. As such, the magnetic label may specifically bind to the capture probe through the specific binding interaction between streptavidin and biotin. Other types of binding interactions are also possible. For example, the magnetic label may be functionalized with biotin and the capture probe may be functionalized with streptavidin. Alternatively, the magnetic label and the capture probe may be functionalized with complementary members of other specific binding pairs, as described above.

In some instances, the magnetic label is stably associated with one member of a binding pair. By "stably associated" is meant that the magnetic label and the member of the binding pair maintain their position relative to each other in space under the conditions of use, e.g., under the assay conditions. As such, the magnetic label and the member of the binding pair can be non-covalently or covalently stably associated with each other. Examples of non-covalent association include non-specific adsorption, binding based on electrostatic (e.g., ion-ion pair interactions), hydrophobic interactions, hydrogen bonding interactions, and the like. Examples of covalent binding include covalent bonds formed between the member of the binding pair and a functional group present on the surface of the magnetic label.

In certain embodiments, the magnetic labels are colloidal. The terms "colloid" or "colloidal" refer to a mixture in which one substance is dispersed throughout another substance. Colloids include two phases, a dispersed phase and a continuous phase. In some instances, colloidal magnetic labels remain dispersed in solution and do not precipitate or settle out of solution. Colloidal magnetic labels that remain dispersed in solution may facilitate a minimization in background signals and non-specific interaction of the magnetic labels with the magnetic sensor or inter-element area. For example, the methods may include contacting a magnetic sensor with an assay composition that includes a sample and a magnetic label, such that an analyte of interest in the sample is bound to the surface of the magnetic sensor or inter-element area. Because the colloidal magnetic labels remain dispersed in solution, the magnetic labels are not positioned near enough to the magnetic sensor to induce a detectable signal in the magnetic sensor, which facilitates a minimization in background signals. In some cases, specific binding of the magnetic labels to the surface-bound analyte positions the magnetic label near the magnetic sensor, such that a detectable signal is induced in the magnetic sensor.

Magnetic labels that may be employed in various methods (e.g., as described herein) may vary, and include any type of label that induces a detectable signal in a magnetic sensor when the magnetic label is positioned near the surface of the magnetic sensor. For example, magnetic labels may include, but are not limited to, magnetic labels, optical labels (e.g., surface enhanced Raman scattering (SERS) labels), fluorescent labels, and the like. Each of these types of magnetic labels is discussed in more detail below.

Magnetic labels are labeling moieties that, when sufficiently associated with a magnetic sensor or inter-element area, are detectable by the magnetic sensor and cause the magnetic sensor to output a signal. For example, the presence of a magnetic label near the magnetic sensor may induce a detectable change in the magnetic sensor, such as, but not limited to, a change in resistance, conductance, inductance, impedance, etc. In some cases, the presence of a magnetic label near the magnetic sensor induces a detectable change in the resistance of the magnetic sensor. Magnetic labels of interest may be sufficiently associated with a magnetic sensor if the distance between the center of the magnetic label and the magnetic sensor is 1000 nm or less, such as 800 nm or less, such as 400 nm or less, including 100 nm or less.

In certain instances, the magnetic labels include one or more materials selected from paramagnetic, superparamagnetic, ferromagnetic, ferromagnetic, antiferromagnetic materials, combinations thereof, and the like. For example, the magnetic labels may include superparamagnetic materials. In certain embodiments, the magnetic labels are configured to be nonmagnetic in the absence of an external magnetic field. By "nonmagnetic" is meant that the magnetization of a magnetic labels is zero or averages to zero over a certain period of time. In some cases, the magnetic label may be nonmagnetic due to random flipping of the magnetization of the magnetic label over time. Magnetic labels that are configured to be nonmagnetic in the absence of an external magnetic field may facilitate the dispersion of the magnetic labels in solution because nonmagnetic labels do not normally agglomerate in the absence of an external magnetic field or even in the presence of a small magnetic field in which thermal energy is still dominant. In certain embodiments, the magnetic labels include superparamagnetic materials or synthetic antiferromagnetic materials. For instance, the magnetic labels may include two or more layers of antiferromagnetically-coupled ferromagnets.

In certain embodiments, the magnetic labels are high moment magnetic labels. The magnetic moment of a magnetic label is a measure of its tendency to align with an external magnetic field. By "high moment" is meant that the magnetic labels have a greater tendency to align with an external magnetic field. Magnetic labels with a high magnetic moment may facilitate the detection of the presence of the magnetic labels near the surface of the magnetic sensor because it is easier to induce the magnetization of the magnetic labels with an external magnetic field.

In certain embodiments, the magnetic labels include, but are not limited to, Co, Co alloys, ferrites, cobalt nitride, cobalt oxide, Co—Pd, Co—Pt, iron, iron oxides, iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, Ni alloys, combinations thereof, and the like. Examples of high moment magnetic labels include, but are not limited to, Co, Fe or CoFe nanocrystals, which may be superparamagnetic at room temperature, and synthetic antiferromagnetic nanoparticles.

In some embodiments, the surface of the magnetic label is modified. In certain instances, the magnetic labels may be coated with a layer configured to facilitate stable association of the magnetic label with one member of a binding pair, as described above. For example, the magnetic label may be coated with a layer of gold, a layer of poly-L-lysine modified glass, dextran, and the like. In certain embodiments, the magnetic labels include one or more iron oxide cores imbedded in a dextran polymer. Additionally, the surface of the magnetic label may be modified with one or more surfactants. In some cases, the surfactants facilitate an increase in the water solubility of the magnetic labels. In certain embodiments, the surface of the magnetic labels is modified with a passivation layer. The passivation layer may facilitate the chemical stability of the magnetic labels in the assay conditions. For example, the magnetic labels may be coated with a passivation layer that includes gold, iron oxide, polymers (e.g., polymethylmethacrylate films), and the like.

In certain embodiments, the magnetic labels have a spherical shape. Alternatively, the magnetic labels can be disks, rods, coils, or fibers. In some cases, the size of the magnetic labels is such that the magnetic labels do not interfere with the binding interaction of interest. For example, the magnetic labels may be comparable to the size of the analyte and the capture probe, such that the magnetic labels do not interfere with the binding of the capture probe to the analyte. In some cases, the magnetic labels are magnetic nanoparticles, or contain multiple magnetic nanoparticles held together by a suitable binding agent. In some embodiments, the average diameter of the magnetic labels is from 5 nm to 250 nm, such as from 5 nm to 150 nm, including from 10 nm to 100 nm, for example from 25 nm to 75 nm. For example, magnetic labels having an average diameter of 5 nm, 10 nm, 20 nm, 25 nm, 30 nm, 35 nm, 40 nm, 45 nm, 50 nm, 55 nm, 60 nm, 70 nm, 80 nm, 90 nm, or 100 nm, as well as magnetic labels having average diameters in ranges between any two of these values, may be used with the subject methods. In some instances, the magnetic labels have an average diameter of 50 nm.

Magnetic labels and their conjugation to biomolecules are further described in U.S. Application Publication No. 2009/0104707, filed Sep. 19, 2008, the disclosure of which is hereby incorporated by reference in its entirety.

Assay Composition Production

In some instances, the method includes producing the assay composition by sequentially contacting the magnetic sensor array (e.g., array of biosensors) with the sample and the magnetic label. For example, the method may include contacting the magnetic sensor array first with the sample and subsequently with the magnetic label. Alternatively, the method may include contacting the magnetic sensor array first with the magnetic label and subsequently with the sample.

In other embodiments, the method includes combining the sample and the magnetic label to produce the assay composition and then contacting the magnetic sensor array with the assay composition. For instance, the method may include first combining the sample and the magnetic label to produce the assay composition. Then the magnetic sensor may be contacted with the assay composition, as described above. Subsequently, the method may include contacting the magnetic sensor with the capture probe, as described in detail below.

Capture Probe

A capture probe can be any molecule that specifically binds to a protein or nucleic acid sequence that is being targeted (e.g., the analyte of interest). Depending on the nature of the analyte, capture probes can be, but are not limited to, (a) single strands of DNA complementary to a unique region of the target DNA or RNA sequence for the detection of nucleic acids; (b) antibodies against an epitope of the peptidic analyte for the detection of proteins and peptides; (c) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like.

In certain embodiments, the capture probe includes an antibody. The capture probe antibody may specifically bind to an analyte of interest. In some cases, the capture probe is a modified antibody. The modified antibody may be configured to specifically bind to the analyte of interest and may also include one or more additional members of a specific binding pair. The one or more members of a specific binding pair may be configured to specifically bind to a complementary member of the specific binding pair. In certain instances, the complementary member of the specific binding pair is bound to the magnetic label, as described above. For example, the capture probe may be an antibody that specifically binds to an analyte of interest. In addition, the capture probe may be modified to include biotin. As described above, in certain embodiments, magnetic labels may be modified to include streptavidin. As such, the capture probe may be configured to specifically bind to the analyte of interest (e.g., through an antibody-antigen interaction) and to specifically bind to the magnetic label (e.g., through a streptavidin-biotin interaction). In some cases, the capture probe is configured to bind to the analyte of interest and the magnetic label. Stated another way, the capture probe may be configured such that specific binding of the analyte to the capture probe does not significantly interfere with the ability of the capture probe to specifically bind to the magnetic label. Similarly, the capture probe may be configured such that specific binding of the magnetic label to the capture probe does not significantly interfere with the ability of the capture probe to specifically bind to the analyte.

In certain embodiments, the capture probe specifically binds to an analyte of interest. In some cases, the capture probe can be identified so that the presence of the analyte of interest can then be detected. Capture probes may be identified by any of the methods described herein. For example, as described above, analytes may be directly or indirectly bound to a magnetic sensor or inter-element area. The capture probe may contact and specifically bind to the analyte of interest. As indicated above, the capture probe may be configured to bind to a magnetic label and the analyte of interest. In certain instances, simultaneous binding of the capture probe to surface-bound analyte and the magnetic label positions the magnetic label within the detection range of the magnetic sensor, such that a detectable signal is induced in the magnetic sensor.

In some cases, false-positive signals due to non-specific binding of the capture probe to moieties not of interest are minimized. For example, non-specific binding of the capture probe to other moieties not of interest, which are not bound to the surface of the magnetic sensor array and remain in solution, will not induce a detectable or non-negligible signal in the magnetic sensor because the magnetic label bound to the capture probe will not be positioned within the detection range of the magnetic sensor.

As described above, the magnetic label may be colloidal, such that the magnetic label remains dispersed in the assay composition solution. In certain instances, the kinetics of the capture probe diffusion to the surface of the magnetic sensor and binding to the analyte is significantly faster than the kinetics of the diffusion of the magnetic labels to the surface of the magnetic sensor. Having faster kinetics for the binding of the capture probe to the analyte than the diffusion of the magnetic label to the surface of the magnetic sensor array may facilitate a minimization in false positive signals due to non-specific positioning of the magnetic label within the detection range of the magnetic sensor.

In certain embodiments, the magnetic sensor arrays are contacted with the capture probe after the magnetic sensor arrays are contacted with the assay composition. Thus, the methods may include first producing an assay composition that includes a sample and a magnetic label. The magnetic sensor array may then be contacted with the assay composition. Subsequently, the magnetic sensor array may be contacted with a capture probe.

Other methods are also possible. For example, the method may include first contacting the magnetic sensor arrays to the capture probe, and subsequently contacting the magnetic sensor arrays to the assay composition, where the assay composition includes a sample and a magnetic label. In both of the methods described above, the magnetic label is present in the assay composition prior to contacting the magnetic sensor array to the capture probe.

As described above, in some instances, the methods are wash-free methods of evaluating the presence of one or more analytes in a sample. As such, in certain embodiments, contacting the magnetic sensor arrays with assay components does not include any washing steps before or after contacting the magnetic sensor arrays with each component of the assay composition. Thus, no washing step is performed either before or after the magnetic sensor is contacted with any of the assay components.

Obtaining a Signal to Determine Whether an Analyte is Present in a Sample

Embodiments of the subject methods also include obtaining a signal from a magnetic sensor to detect the presence of an analyte in a sample. As described above, a magnetic label may be bound, either directly or indirectly, to the analyte, which in turn may be bound, either directly or indirectly, to the magnetic sensor. If the bound magnetic label is positioned within the detection range of the magnetic sensor, then the magnetic sensor may provide a signal indicating the presence of the bound magnetic label, and thus indicating the presence of the analyte.

Magnetic sensors may be configured to generate an electrical signal in response to a magnetic label in proximity to the magnetic sensor. For example, a change in the resistance of the magnetic sensor may be induced by changes in the local magnetic field. In some cases, binding of a magnetic label (e.g., a magnetic label) in close proximity to the magnetic sensor induces a detectable change in the local magnetic field of the magnetic sensor. For example, the magnetic field created by the magnetic labels that are bound to the analytes of interest may exceed the magnetic field that is created by unbound magnetic labels that remain dispersed in the sample. Changes in the local magnetic field of the magnetic sensor may be detected as a change in the resistance of the magnetic sensor. In certain embodiments, unbound magnetic labels do not produce a detectable signal in the magnetic sensor.

Utility

The subject systems and methods find use in a variety of different applications where determination of the presence or absence, and/or quantification of one or more analytes in a sample is desired. The subject systems and methods also find use in applications where the screening of a plurality of samples is desired. In certain embodiments, the methods are directed to detection of a set of biomarkers, e.g., two or more distinct protein biomarkers, in a plurality of samples. For example, the methods may be used in the rapid detection of two or more disease biomarkers in a group of serum samples, e.g., as may be employed in the diagnosis of a disease condition in a subject, in the ongoing management or treatment of a disease condition in a subject, etc.

In certain embodiments, the subject systems and methods find use in detecting biomarkers. In some cases, the subject systems and methods may be used to detect the presence or absence of particular biomarkers, as well as an increase or decrease in the concentration of particular biomarkers in blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject methods and systems. Furthermore, the early detection of biomarkers associated with diseases is facilitated by the picomolar and/or femtomolar sensitivity of the subject methods and systems. Due to the capability of detecting multiple biomarkers on a single magnetic sensor device, the presently disclosed assay systems and methods finds use in screening of a plurality of samples in multiplexed molecular diagnostics.

In certain embodiments, the subject systems and methods find use in detecting biomarkers for a disease or disease state. In some cases, the disease is a cellular proliferative disease, such as but not limited to, a cancer, a tumor, a papilloma, a sarcoma, or a carcinoma, and the like. Thus, the subject systems and methods find use in detecting the presence of a disease, such as a cellular proliferative disease, such as a cancer, tumor, papilloma, sarcoma, carcinoma, or the like. In certain embodiments, the subject systems and methods find use in detecting biomarkers for an infectious disease or disease state. In some cases, the biomarkers can be molecular biomarkers, such as but not limited to proteins, nucleic acids, carbohydrates, small molecules, and the like. Similarly, the subject methods, systems and kits can be used to detect cardiovascular diseases, central nervous diseases, kidney failures, diabetes, autoimmune diseases, and many other diseases.

For example, in certain embodiments, the subject systems and methods find use in detecting biomarkers, such as carcinoembryonic antigen (cancer embryonic antigen; CEA). CEA refers to a set of highly related glycoproteins involved in cell adhesion, which is normally produced in gastrointestinal tissue during fetal development, but the production stops before birth. Therefore, CEA is usually present only at very low levels in the blood of healthy adults. However, the serum levels of CEA may be elevated in some types of cancer, and thus can be used as a tumor biomarker in clinical assays.

In certain embodiments, the subject methods, systems and kits can be used to detect the presence or absence, and/or quantification of one or more analytes in a plurality of samples for food and/or environmental safety. For example, the subject systems and methods can be used to determine the presence of analytes in a plurality of samples of potentially contaminated water, soil or food, such as for the detection of infectious disease agents, e.g., bacteria, viruses, molds, etc., including potential biological warfare agents.

Computer Related Embodiments

A variety of computer-related embodiments are also provided. Specifically, the data analysis methods described in the previous sections may be performed using a computer. Accordingly, provided is a computer-based system for analyzing data produced using the above methods in order to provide qualitative and/or quantitative determination of a binding interaction of interest.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, DVD-ROM, BD-ROM, a hard disk drive, a ROM or integrated circuit, a magneto-optical disk, a solid-state memory device, a computer readable card such as a PCMCIA card, and the like, whether or not such devices are internal or external to the computer. A file containing information may be "stored" on computer readable medium, where "storing" means recording information such that it is accessible and retrievable at a later date by a computer. Examples of media include, but are not limited to, non-transitory media, e.g., physical media in which the programming is associated with, such as recorded onto, a physical structure. Non-transitory media does not include electronic signals in transit via a wireless protocol.

In certain embodiments, computer programming may include instructions for directing a computer to perform one or more assay steps to determine the presence of an analyte of interest in a sample. For example, the computer programming may include instructions for directing a computer to determine whether an analyte is present in a sample, e.g., determining the presence or absence of one or more analytes in a sample. In certain embodiments, the computer programming includes instructions for directing a computer to determine the presence of one or more analytes in the sample qualitatively and/or quantitatively. As described above, qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In some embodiments, the computer programming includes instructions for directing a computer to perform a uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the computer programming includes instructions for directing a computer to perform a uniplex analysis of the sample to determine the presence of the analyte of interest in the sample mixture.

In certain embodiments, the computer programming includes instructions for directing a computer to perform a multiplex analysis of two or more analytes in a sample. By "multiplex analysis" is meant that the presence of two or more distinct analytes, in which the two or more analytes are different from each other, is determined. For example, analytes may include detectable differences in their molecular structure, sequence, and the like, as described above. In some instances, the number of analytes is greater than 2, such as 4 or more, 6 or more, 8 or more, etc., up to 20 or more, e.g., 50 or more, including 100 or more, or 1000 or more distinct analytes. In certain embodiments, the computer programming includes instructions for directing a computer to perform a multiplex analysis of 2 to 1000 distinct analytes, such as 4 to 500 distinct analytes, including 4 to 200 distinct analytes, or 4 to 100 distinct analytes, or 4 to 50 distinct analytes, or 4 to 20 distinct analytes. In certain embodiments, the computer programming includes instructions for directing a computer to perform several multiplex assays in parallel substantially simultaneously.

With respect to computer readable media, "permanent memory" refers to memory that is permanent. Permanent memory is not erased by termination of the electrical supply to a computer or processor. Computer hard-drive, CD-ROM, DVD-ROM, BD-ROM, solid state memory and floppy disk are all examples of permanent memory. Random Access Memory (RAM) is an example of non-permanent memory. A file in permanent memory may be editable and re-writable.

Kits

Also provided are kits for practicing one or more embodiments of the above-described methods. The subject kits may vary, and may include various devices and reagents. Reagents and devices include those mentioned herein with respect to magnetic sensor devices or components thereof (such as a magnetic sensor array), magnetic labels, capture probes, analyte-specific probes, buffers, etc. The reagents, magnetic labels, capture probes, etc. may be provided in separate containers, such that the reagents, magnetic labels, capture probes, etc. may be used individually as desired. Alternatively, one or more reagents, magnetic labels, capture probes, etc. may be provided in the same container such that the one or more reagents, magnetic labels, capture probes, etc. is provided to a user pre-combined.

In certain embodiments, the kits include a magnetic sensor device as described above, and a magnetic label. For example, the magnetic label may be a magnetic nanoparticle, as described above.

In some instances, the kits include at least reagents finding use in the methods (e.g., as described above); and a computer readable medium having a computer program stored thereon, wherein the computer program, when loaded into a computer, operates the computer to qualitatively and/or quantitatively determine a binding interaction of interest from a real-time signal obtained from a magnetic sensor; and a physical substrate having an address from which to obtain the computer program.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Bluray, computer readable memory device (e.g., a flash memory drive), etc., on which the information has been recorded. Yet another means that may be present is a website address which may be used via the Internet to access the information at a removed site. Any convenient means may be present in the kits.

Although the foregoing embodiments has been described in some detail by way of illustration and example for purposes of clarity of understanding, it is readily apparent to those of ordinary skill in the art in light of the teachings of this present disclosure that certain changes and modifications may be made thereto without departing from the spirit or scope of the appended claims.

Accordingly, the preceding merely illustrates the principles of embodiments of the present disclosure. It will be appreciated that those skilled in the art will be able to devise various arrangements which, although not explicitly described or shown herein, embody the principles of the subject embodiments and are included within its spirit and scope. Furthermore, all examples and conditional language recited herein are principally intended to aid the reader in understanding the principles of embodiments of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

That which is claimed is:

1. A magnetic sensor comprising:
a magnetic sensor element comprising a sensor surface modification;
an inter-element area adjacent to the magnetic sensor element and comprising an inter-element area surface modification; and
a support,
wherein the inter-element area surface modification has a binding surface configured to bind a magnetic label,
wherein the magnetic sensor element and the inter-element area are coplanar and arranged on an external surface of the support,
wherein the sensor surface modification and the inter-element area surface modification are arranged on an external surface of the magnetic sensor,
wherein the inter-element area has a top surface that is at a depth below the top surface of the magnetic sensor element, and
wherein the inter-element area comprises a side surface of the magnetic sensor element comprising a side surface modification facing an interior volume of the inter-element area.

2. The magnetic sensor of claim 1, wherein the sensor surface modification and the inter-element area surface modification comprise different surface modifications.

3. The magnetic sensor of claim 2, wherein the sensor surface modification and the inter-element area surface modification comprise different chemical compositions.

4. The magnetic sensor of claim 3, wherein the sensor surface modification comprises a layer of a metal on a surface of the magnetic sensor element and the inter-element area surface modification comprises a layer of a dielectric material on a surface of the inter-element area.

5. The magnetic sensor of claim 3, wherein the sensor surface modification comprises a layer of a dielectric material on a surface of the magnetic sensor element and the inter-element area surface modification comprises a layer of a metal on a surface of the inter-element area.

6. The magnetic sensor of claim 5, wherein the dielectric material comprises silicon dioxide and the metal comprises gold.

7. The magnetic sensor of claim 1, wherein the side surface modification is different from the sensor surface modification.

8. The magnetic sensor of claim 1, wherein the side surface modification is different from the inter-element area surface modification.

9. The magnetic sensor of claim 1, wherein the side surface modification is the same as the inter-element area surface modification.

10. The magnetic sensor of claim 1, wherein the side surface modification has a thickness of 15 nm to 150 nm.

11. The magnetic sensor of claim 7, wherein the sensor surface modification and the inter-element area surface modification each comprise a layer of a dielectric material and the side surface modification of the magnetic sensor comprises a layer of a metal.

12. The magnetic sensor of claim 11, wherein the dielectric material comprises silicon dioxide and the metal comprises gold.

13. The magnetic sensor of claim 1, wherein the sensor surface modification comprises a cover on a surface of the magnetic sensor element.

14. The magnetic sensor of claim 1, wherein a width of the inter-element area is 0.5 times or more a width of the magnetic sensor element.

15. The magnetic sensor of claim 1, wherein a length of the magnetic sensor element is 1.5 times or more a width of the magnetic sensor element.

16. The magnetic sensor of claim 1, wherein the inter-element area has a depth of 25 nm or more.

17. The magnetic sensor of claim 1, wherein the magnetic sensor element comprises a reference layer with a magnetization substantially parallel to a width of the magnetic sensor element.

18. A magnetic sensor system comprising:
a magnetic sensor device comprising:
a magnetic sensor array comprising two or more magnetic sensors each comprising:
a magnetic sensor element comprising a sensor surface modification; and
an inter-element area adjacent to the magnetic sensor element and comprising an inter-element area surface modification; and
a support,
wherein the inter-element area surface modification has a binding surface configured to bind a magnetic label,
wherein the magnetic sensor element and the inter-element area are coplanar and arranged on an external surface of the support,
wherein the sensor surface modification and the inter-element area surface modification are arranged on an external surface of the magnetic sensor;
wherein the inter-element area has a top surface that is at a depth below the top surface of the magnetic sensor element, and
wherein the inter-element area comprises a side surface of the magnetic sensor element comprising a side surface modification facing an interior volume of the inter-element area; and
a magnetic field source.

19. The magnetic sensor system of claim 18, further comprising a processor configured to obtain an analyte-specific signal from the magnetic sensor device.

20. A kit comprising:
a magnetic sensor device comprising:
a magnetic sensor array comprising two or more magnetic sensors according to claim 1; and
a magnetic label.

21. The magnetic sensor of claim 1, wherein the inter-element area surface modification comprises an analyte-specific probe configured to bind the magnetic label.

22. The magnetic sensor of claim 21, wherein the analyte-specific probe is a surface capture ligand.

23. The magnetic sensor of claim 1, further comprising a second magnetic sensor element comprising a second sensor surface modification, wherein the inter-element area is adjacent to and located between the magnetic sensor element and the second magnetic sensor element.

24. The magnetic sensor of claim 1, wherein the magnetic sensor element comprises a giant magnetoresistive (GMR) element or a tunneling magnetoresistive (TMR) element.

25. The magnetic sensor of claim 1, wherein the inter-element area does not include a giant magnetoresistive (GMR) element or a tunneling magnetoresistive (TMR) element.

26. The magnetic sensor of claim 1, wherein the sensor surface modification has a binding surface.

27. The magnetic sensor of claim 1, wherein the side surface modification comprises an analyte-specific probe configured to bind the magnetic label.

* * * * *